US010436789B2

(12) United States Patent
Branch et al.

(10) Patent No.: US 10,436,789 B2
(45) Date of Patent: Oct. 8, 2019

(54) HCV CORE AND MINICORE BINDING MOLECULES

(71) Applicant: Icahn School of Medicine at Mount Sinai, New York, NY (US)

(72) Inventors: Andrea Branch, New York, NY (US); Francis Eng, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 16/227,104

(22) Filed: Dec. 20, 2018

(65) Prior Publication Data

US 2019/0170753 A1  Jun. 6, 2019

Related U.S. Application Data

(63) Continuation of application No. PCT/US2017/038696, filed on Jun. 22, 2017.

(60) Provisional application No. 62/353,142, filed on Jun. 22, 2016.

(51) Int. Cl.
| | |
|---|---|
| *G01N 33/53* | (2006.01) |
| *A61K 39/00* | (2006.01) |
| *G01N 21/00* | (2006.01) |
| *G01N 21/64* | (2006.01) |
| *G01N 33/68* | (2006.01) |
| *G01N 33/576* | (2006.01) |
| *C07K 16/10* | (2006.01) |

(52) U.S. Cl.
CPC ....... *G01N 33/5767* (2013.01); *C07K 16/109* (2013.01); *C07K 2317/34* (2013.01); *C07K 2317/565* (2013.01); *G01N 2333/186* (2013.01)

(58) Field of Classification Search
CPC ..... G01N 21/6428; G01N 2201/06113; G01N 2201/062; G01N 15/1429; A61K 39/39558

See application file for complete search history.

(56) References Cited

U.S. PATENT DOCUMENTS

| | | | |
|---|---|---|---|
| 2010/0291545 | A1 | 11/2010 | Wakita et al. |
| 2011/0008369 | A1 | 1/2011 | Finnefrock et al. |
| 2014/0272931 | A1 | 9/2014 | Ziemann et al. |
| 2017/0052184 | A1 | 2/2017 | Ziemann et al. |

FOREIGN PATENT DOCUMENTS

| | | |
|---|---|---|
| WO | 2015157238 | 10/2015 |
| WO | WO2015157238 | * 10/2015 |

OTHER PUBLICATIONS

International Search Report and Written Opinion of the International Searching Authority for PCT/US2017/038696, dated Oct. 5, 2017, 13 pages.

* cited by examiner

*Primary Examiner* — Barry A Chestnut
(74) *Attorney, Agent, or Firm* — Heslin Rothenberg Farley and Mesiti, PC; Kathy Smith Dias

(57) ABSTRACT

The present disclosure relates to hepatitis C virus (HCV) core and minicore-binding molecules and nucleic acid sequences encoding such molecules. In particular embodiments, the present invention provides HCV core and minicore-binding molecules (e.g., monoclonal antibodies or antibody fragments) with particular light chain and/or heavy chain CDRs (e.g., selected from SEQ ID NOS: 2-4 and 6-8) and methods for using such molecules to detect the presence of HCV core proteins (e.g., mature p21 core protein or minicore proteins) in a sample.

24 Claims, 9 Drawing Sheets

Specification includes a Sequence Listing.

A. (SEQ ID NO: 1) Amino acid sequence of Neo4 light chain variable domain:

(CDRL1, SEQ ID NO:2)          (CDRL2, SEQ ID NO:3)

DIVLTQSPASLIVSLGQRATISC<u>RASKSVNEYGYTYMH</u>WYQQKPGLPPKLLIY<u>LASNLDSGV</u>PARFS
GSGSGTDFTLNIHPVEEEDAATYYC<u>QHSRELPYT</u>FGGGTKLEIKR
                         (CDRL3, SEQ ID NO:4)

B. (SEQ ID NO: 5) Amino acid sequence of Neo4 heavy chain variable domain sequence:

(CDRH1, SEQ ID NO:6)         (CDRH2, SEQ ID NO:7)

QIQLKESGPAVIKPSQSLSLTCIVS<u>GFSITSSVYC</u>WQWIRQPPGKGLEWMG<u>RICYDGSVDYSPSITSR</u>
GTISRDTSLNKVFFQLSSVTNEDTAMYYCSR<u>ENHIDYYDTTYPSFDV</u>WGAGTTVTVSS
                          (CDRH3, SEQ ID NO:8)

FIGURE 7

A. (SEQ ID NO:9) Variable light chain nucleotide sequence:

gacattgtgctgacacagtctcctgcttccttaattgtatctctggggcagagggccaccatctcgtgcagggccagcaaaagtgtcaatgaatatggctatacttatatgcact
ggtaccaacagaaaccaggactgccacccaaactcctcatctatcttgcatccaatctagattctggggtccctgccaggttcagtggcagtgggtctgggacagacttcacc
ctcaacatccatcctgtggaggaggaggatgctgcaacctattactgtcaacacagtagggagcttccgtacacgttcggaggggggaccaagctggaaataaaacgg

B. (SEQ ID NO:10) Variable heavy chain nucleotide sequence:

cagattcagctgaaggagtctggacctgctgtcatcaagccatcacagtcactgtctctcacgtgcatagtctctggattctccatcacaagtagtgtttattgctggcagtggat
ccgccagccccaggaaagggattagagtggatgggacgcatctgttatgacggttcagttgactatagtccatccatcacaagccgcggcaccatctccagagacacatc
tctgaacaaagtcttttccagctgagctctgtgacaaatgaggacacagccatgtactactgttccagggaaaaccatattgattactacgatactacttatccgtccttcgatgt
ctggggcgcagggaccacggtcaccgtctcctca

HCV CORE AND MINICORE BINDING MOLECULES

CROSS REFERENCE TO RELATED APPLICATIONS

This application is a continuation of PCT/US2017/038696 filed Jun. 22, 2017 and published on Dec. 28, 2017 as WO 2017/223283, which claims priority to U.S. provisional application No. 62/353,142 filed Jun. 22, 2016; the contents of which are hereby incorporated by reference in their entirety into the present disclosure.

STATEMENT OF RIGHTS UNDER FEDERALLY-SPONSORED RESEARCH

This invention was made with government support under grant numbers DK090317, DA031095 and CA152514 awarded by the National Institutes of Health. The government has certain rights in the invention.

SEQUENCE LISTING

This application contains a Sequence Listing, created on Jun. 14, 2017; the file, in ASCII format, is designated 3710028A_sequencelisting_ST25.txt and is 12 KB in size. The file is hereby incorporated by reference in its entirety into the application.

FIELD OF THE INVENTION

The present invention relates to hepatitis C virus (HCV) core and minicore-binding molecules and nucleic acid sequences encoding such molecules. In particular embodiments, the present invention provides HCV core and minicore-binding molecules (e.g., monoclonal antibodies or antibody fragments) with particular light chain and/or heavy chain CDRs (e.g., selected from SEQ ID NOS: 2-4 and 6-8) and methods for using such molecules to detect the presence of HCV core proteins (e.g., mature p21 core protein or minicore proteins) in a sample.

BACKGROUND OF THE INVENTION

The hepatitis C virus chronically infects about 170 million people worldwide. Effective antiviral drug treatments are available. However, because of reinfections, high pharmaceutical costs, and new infections, additional interventions may be needed to bring the global HCV epidemic under control. As a result, there is continued interest in HCV molecular virology, virus-host interactions, and vaccine development.

In 2009, it was discovered that HCV expresses a family of previously-unknown proteins from the core gene (Eng et al., J. Virol., 2009; 83:3104-14; herein incorporated by reference). These minicore proteins have the C-terminal portion of the mature p21 nucleocapsid (core) protein, but lack the N-terminus (see FIG. 1). The estimated sizes of two prominent minicore proteins, 70 and 91 minicore, suggest that they begin at core amino acids 70 and 91, respectively (see FIGS. 1 and 2). Mutations in positions 70 and 91 are associated with an increased risk of hepatocellular carcinoma, insulin resistance, and failure on interferon-based treatments (see Akuta et al., Hepatology, 2007, 46:1357-64; Akuta et al., J. Med. Virol., 2009, 81:1032-9; and Akuta et al., J. Hepatol. 2007, 46:403-10; all of which are herein incorporated by reference), suggesting that minicores may affect clinical outcomes. It was recently found that minicores are secreted into the media in cell culture systems (El-Shamy et al., Hepatology, 2014; 60:1056A; #1782).

SUMMARY OF THE INVENTION

The present invention relates to HCV core and minicore-binding molecules and nucleic acid sequences encoding such molecules. In particular embodiments, the present invention provides HCV core and minicore-binding molecules (e.g., monoclonal antibodies or antibody fragments) with particular light chain and/or heavy chain CDRs (e.g., selected from SEQ ID NOS: 2-4 and 6-8) and methods for using such molecules to detect the presence of HCV core proteins (e.g., mature p21 core protein, and 70 and 91 minicore proteins) in a sample.

In some embodiments, provided herein are compositions comprising an HCV core protein binding molecule (e.g., antibody or antibody fragment), or a nucleic acid sequence encoding an HCV core protein binding molecule, wherein the HCV core protein binding molecule comprises: at least one CDR sequence selected from the group consisting of: SEQ ID NO: 2, SEQ ID NO: 2 with one or more conservative or non-conservative amino acid changes, SEQ ID NO: 3, SEQ ID NO: 3 with one or more conservative or non-conservative amino acid changes, SEQ ID NO: 4, SEQ ID NO: 4 with one or more conservative or non-conservative amino acid changes, SEQ ID NO: 6, SEQ ID NO: 6 with one or more conservative or non-conservative amino acid changes, SEQ ID NO: 7, SEQ ID NO: 7 with one or more conservative or non-conservative amino acid changes, SEQ ID NO: 8, and SEQ ID NO: 8 with one or more conservative or non-conservative amino acid changes.

In certain embodiments, provided herein are compositions comprising an HCV core protein-binding molecule, wherein the HCV core protein-binding molecule comprises: a) a light chain variable region (or a portion of a light chain variable region), wherein the light chain variable region comprises; i) a CDRL1 amino acid sequence selected from the group consisting of SEQ ID NO: 2 and SEQ ID NO: 2 with one or more conservative or non-conservative amino acid changes; ii) a CDRL2 amino acid sequence selected from the group consisting of SEQ ID NO: 3 and SEQ ID NO: 3 with one or more conservative or non-conservative amino acid changes; and iii) a CDRL3 amino acid sequence selected from the group consisting of SEQ ID NO: 4 and SEQ ID NO: 4 with one or more conservative or non-conservative amino acid changes; and b) a heavy chain variable region (or a portion of a heavy chain variable region), wherein the heavy chain variable region comprises; i) a CDRH1 amino acid sequence selected from the group consisting of SEQ ID NO: 6 and SEQ ID NO: 6 with one or more conservative or non-conservative amino acid changes; ii) a CDRH2 amino acid sequence selected from the group consisting of SEQ ID NO: 7 and SEQ ID NO: 7 with one or more conservative or non-conservative amino acid changes; and iii) a CDRH3 amino acid sequence selected from the group consisting of SEQ ID NO: 8 and SEQ ID NO: 8 with one or more conservative or non-conservative amino acid changes.

In other embodiments, provided herein are compositions comprising: a nucleic acid sequence encoding a light chain variable region (or portion of a light chain variable region), wherein the light chain variable region comprises; i) a CDRL1 amino acid sequence selected from the group consisting of SEQ ID NO: 2 and SEQ ID NO: 2 with one or more conservative amino acid changes; ii) a CDRL2 amino acid sequence selected from the group consisting of SEQ ID NO: 3 and SEQ ID NO: 3 with one or more conservative amino acid changes; and iii) a CDRL3 amino acid sequence selected from the group consisting of SEQ ID NO: 4 and SEQ ID NO: 4 with one or more conservative amino acid changes. In some embodiments, the nucleic acid sequence encoding the light chain variable region is as shown in SEQ ID NO: 9 or a nucleic acid sequence with at least 85% or 95% sequence identity with SEQ ID NO: 9. In other embodiments, provided herein are compositions comprising a nucleic acid sequence encoding a heavy chain variable region (or at least a portion of a heavy chain variable region), wherein the heavy chain variable region comprises; i) a CDRH1 amino acid sequence selected from the group consisting of SEQ ID NO: 6 and SEQ ID NO: 6 with one or more conservative or non-conservative amino acid changes; ii) a CDRH2 amino acid sequence selected from the group consisting of SEQ ID NO: 7 and SEQ ID NO: 7 with one or more conservative or non-conservative amino acid changes; and iii) a CDRH3 amino acid sequence selected from the group consisting of SEQ ID NO: 8 and SEQ ID NO: 8 with one or more conservative or non-conservative amino acid changes. In certain embodiments, the nucleic acid sequence encoding the heavy chain variable region is as shown in SEQ ID NO: 10, or a nucleic acid sequence with at least 85% or 95% sequence identity with SEQ ID NO: 10. In other embodiments, the compositions comprise a nucleic acid sequence, or sequences, encoding both the light and heavy chain variable regions. In other embodiments, the compositions further comprise an expression vector wherein the nucleic acid sequences of the light and heavy chain variable regions are present in the expression vector.

In certain embodiments, the HCV core protein binding molecule is an antibody or antibody fragment that has one or more of the following characteristics: i) is a monoclonal antibody; ii) is a chimeric, a humanized or a fully human antibody; iii) is an antibody of the IgG1-, IgG2-, IgG3- or IgG4-type; iv) is a Fab fragment, a Fab' fragment, an F(ab')2 fragment, or an Fv fragment; and v) is labeled. In additional embodiments, the HCV core protein binding molecule is an antibody or antibody fragment capable of binding HCV p21 core protein and/or HCV 70 or 91 minicore protein. In certain embodiments, the antibody comprises the Neo4 antibody or antigen-binding fragment of the Neo4 antibody.

In particular embodiments, the light and/or heavy chain variable region comprises a mouse or human framework region. In other embodiments, the HCV core protein binding molecule has a higher binding affinity for p21 core or a minicore protein than monoclonal antibody C11-3 (ABT-4). In certain embodiments, the HCV core protein binding molecule has a binding affinity that is at least 1.5 times that of C11-3 (e.g., 1.5 . . . 2.0 . . . 3.0 . . . 10.0 . . . or . . . 15 times). In certain embodiments, the HCV core protein binding molecule is capable of binding HCV p21 core protein. In other embodiments, the HCV core protein binding molecule is capable of binding HCV 70 or 91 minicore protein.

In some embodiments, provided herein are methods of detecting an HCV core protein in a sample comprising: a) contacting a sample with an HCV core protein binding molecule as described herein, wherein the sample is suspected of containing an HCV core protein, and wherein the HCV core protein binding molecule forms a complex with the HCV core protein if present in the sample; and b) detecting the presence or absence of the complex in the sample. In a relates In certain embodiments, the HCV core protein binding molecule comprises a detectable label. In further embodiments, the HCV core protein comprises mature p21 core protein. In other embodiments, the HCV core protein comprises 70 and/or 91 minicore protein. In other embodiments, the methods further comprise contacting the sample with a detection molecule capable of binding to the HCV core protein binding molecule, wherein the detection molecule comprises a detectable label. In some embodiments, the conjugate molecule comprises an anti-mouse antibody or antibody fragment. In certain embodiments, the conjugate molecule comprises a conjugate peptide (e.g., a labeled peptide). In some embodiments, the conjugate peptide comprises at least 5 (e.g., at least 5 . . . 10 . . . 20 . . . or 25) consecutive amino acids from the following amino acid sequence: SPRGSRPSWGPTDPRRRSRNLGKVI (SEQ ID NO: 36).

In certain embodiments, the HCV core protein-binding molecules are attached to a binding molecule (e.g., biotin), where the binding molecule will bind to an attachment molecule (e.g., streptavidin) present on a solid surface (e.g., paramagnetic beads). In such embodiments, the solid surface, such as streptavidin coated beads, and HCV core protein-binding molecules can be added to a sample at, or about, the same time in a capture on the fly system. In such a system, the biotin or other molecule attached to the HCV core protein binding molecule can bind with the streptavidin (or other binding partner) on the beads in solution, and then (or previously) the HCV core binding molecule can bind an HCV core protein in the sample. This forms a complex, on the fly, of the bead attached to the HCV core protein binding molecule, which is attached to a core protein from the sample. The beads (or other solid surface) can then facilitate purification (e.g., magnetic separation). In certain embodiments, the HCV core binding molecule (e.g., an antibody) comprises a detectable label, such as an acridinium compound.

In particular embodiments, the detecting comprises adding a chemiluminescent solution to the sample. In other embodiments, the sample is a purified sample, wherein the purified sample is purified from plasma, serum, or blood. In certain embodiments, the methods further comprise generating the sample by some or all of the following steps: i) contacting a serum sample from a suspected HCV infected patient with a heparin and manganese salt solution to generate an ApoB-associated lipoprotein precipitate, ii) isolating the ApoB-associated lipoprotein precipitate from the remainder of the serum sample; iii) re-suspending the ApoB-associated lipoprotein precipitate in a bicarbonate solution such that a $Mn(HCO_3)_2$ pellet forms and is discarded; iv) dialyzing the ApoB-associated lipoprotein precipitate against a $BaCl_2$ solution such that a $BaCl_2$-heparin precipitate forms and is discarded; v) dialyzing the ApoB-associated lipoprotein precipitate against buffer; vi) applying centrifugal filtration to the ApoB-associated lipoprotein to generate an ApoB-associated lipoprotein concentrate; vii) mixing the ApoB-associated lipoprotein concentrate with an alcohol solution to generate a lipid organic phase and a protein aqueous phase; and viii) separating the protein aqueous phase from the lipid organic phase, and treating the protein aqueous phase such that a protein precipitate is formed, wherein the protein precipitate contains HCV mature core and/or HCV minicore protein. In other embodiments, the methods further comprise generating the sample by using some or all of the following steps: i) contacting a serum sample from a suspected HCV infected patient with a heparin and manganese salt solution to generate an ApoB-associated lipoprotein precipitate, ii) isolating the ApoB-associated lipoprotein precipitate from the remainder of the serum sample; iii) re-suspending the ApoB-associated lipoprotein precipitate in a NaHCO$_3$ solution such that a Mn(HCO$_3$)$_2$ pellet forms and is discarded; iv) dialyzing the ApoB-associated lipoprotein precipitate against a BaCl$_2$ solution such that a BaCl$_2$-heparin precipitate forms and is discarded; v) dialyzing the ApoB-associated lipoprotein precipitate against buffer; vi) applying centrifugal filtration to the ApoB-associated lipoprotein to generate an ApoB-associated lipoprotein concentrate; vii) mixing the ApoB-associated lipoprotein concentrate with butanol and diisopropyl ether to generate a lipid organic phase and a protein aqueous phase; and viii) separating the protein aqueous phase from the lipid organic phase, and treating the protein aqueous phase such that a protein precipitate is formed, wherein the protein precipitate contains HCV mature core and/or HCV minicore protein.

In some embodiments, provided herein are systems or kits comprising: a) an HCV core protein binding molecule as described herein, and b) at least one component selected from the group consisting of: i) a conjugate molecule capable of binding to the HCV core protein binding molecule, wherein the conjugate molecule comprises a detectable label; ii) a control sample containing an HCV core protein; iii) a solid support (e.g., paramagnetic microparticles) capable of binding to the HCV core protein binding molecules; and iv) at least one reagent for purifying an HCV core protein from a sample selected from the group consisting of: A) a heparin and manganese salt solution, B) a bicarbonate solution, C) a BaCl$_2$ solution, D) an alcohol solution (e.g., composed of butanol and diisopropyl), or E) all four of these solutions.

In other embodiments, provided herein are systems comprising: a) an HCV core protein binding molecule as described herein, and b) a sample containing, or suspected of containing, an HCV core protein (e.g., a blood sample, serum sample, plasma sample, or sample purified as described in FIG. 3).

In some embodiments, provided herein are methods of treatment comprising: administering an HCV core protein binding molecule as described herein to a subject, wherein the subject in infected with HCV. In certain embodiments, the HCV core protein binding molecule comprises fully human light and heavy chain framework regions (e.g., humanized antibody or antibody fragment is employed).

In certain embodiments, provided herein are methods of vaccinating a subject against HCV infection comprising: administering a composition to a subject, wherein the composition comprises an immunogenic peptide, wherein the immunogenic peptide comprises amino acids GPTDP (SEQ ID NO: 37) or amino acids LSPRGSRPSWGPT (SEQ ID NO:35).

In other embodiments, the HCV core protein binding molecule comprises a Fab, and further comprises one or more constant regions (e.g., CH2 and/or CH3). In particular embodiments, the HCV core protein binding molecule comprises an antibody (e.g., an antibody comprising a fully human framework with the CDR sequences shown in FIG. 7). In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype.

BRIEF DESCRIPTION OF THE DRAWINGS

FIG. 7 shows the amino acid sequences of Neo4 antibody light and heavy chain variable regions. A shows the light chain CDRs underlined, which include CDRL1 (RASKSVNEYGYTYMH; SEQ ID NO: 2), CDRL2 (LASNLDS; SEQ ID NO: 3), and CDRL3 (QHSRELPYT, SEQ ID NO: 4). B shows the amino acid sequence of Neo4 antibody heavy chain variable region. The heavy chain CDRs are underlined; they include CDRH1 (GFSITSSVYCWQ; SEQ ID NO: 6), CDRH2 (RICYDGSVDYSPSITS; SEQ ID NO: 7), and CDRH3 (ENHIDYYDTTYPSFDV; SEQ ID NO: 8).

FIG. 8 shows the nucleic acid sequences encoding the light and heavy chain variable regions of Neo4. A shows the nucleic acid sequence encoding the light chain variable region of Neo4 (SEQ ID NO: 9), and B shows the nucleic acid sequence encoding the heavy chain variable region of Neo4 (SEQ ID NO: 10).

DETAILED DESCRIPTION OF THE DISCLOSURE

Figure 1:
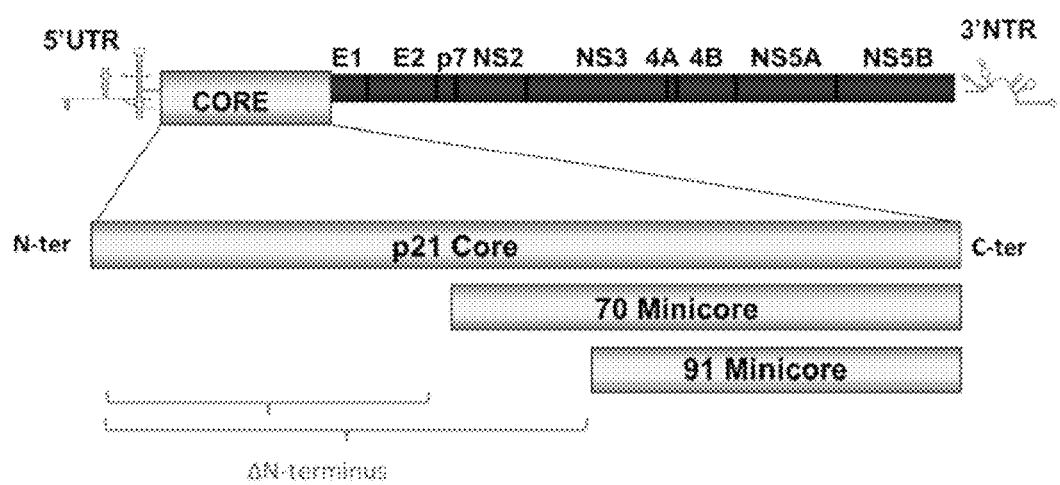
FIG. 1 is a schematic showing the proteins encoded by HCV, including the full-length core p21 protein, and the N-terminally deleted 70 and 91 minicores.

All publications and patents mentioned in the instant specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, medicine, and molecular biology or related fields are intended to be within the scope of the following claims.

Definitions

To facilitate an understanding of the invention, a number of terms are defined below.

The term "antibody," as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each variable region (VH or VL) contains 3 CDRs, designated CDR1, CDR2 and CDR3. Each variable region also contains 4 framework sub-regions, designated FR1, FR2, FR3 and FR4.

As used herein, the term "antibody fragment" refers to a portion of an intact antibody that retains the protein-binding region of the intact antibody. Examples of antibody fragments include, but are not limited to, linear antibodies, single-chain antibody molecules, Fv, Fab and F(ab')$_2$ fragments, and multispecific antibodies formed from antibody fragments. The antibody fragments preferably retain at least part of the heavy and/or light chain variable region.

As used herein, the terms "complementarity determining region" and "CDR" refer to the regions that are primarily responsible for antigen-binding. There are three CDRs in a light chain variable region (CDRL1, CDRL2, and CDRL3), and three CDRs in a heavy chain variable region (CDRH1, CDRH2, and CDRH3). The residues that make up these six CDRs have been characterized by Kabat and Chothia as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; Kabat et al., (1991) Sequences of Proteins of Immunological Interest, 5th Ed. Public Health Service, National Institutes of Health, Bethesda, Md., herein incorporated by reference; and residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region; Chothia and Lesk (1987) J. Mol. Biol. 196: 901-917, herein incorporated by reference. Unless otherwise specified, the terms "complementarity determining region" and "CDR" as used herein, include the residues that encompass both the Kabat and Chothia definitions (i.e., residues 24-34 (CDRL1), 50-56 (CDRL2), and 89-97 (CDRL3) in the light chain variable region; and 26-35 (CDRH1), 50-65 (CDRH2), and 95-102 (CDRH3)). Also, unless specified, as used herein, the numbering of CDR residues is according to Kabat.

As used herein, the term "framework" refers to the residues of the variable region other than the CDR residues as defined herein. There are four separate framework sub-regions that make up the framework: FR1, FR2, FR3, and FR4. In order to indicate if the framework sub-region is in the light or heavy chain variable region, an "L" or "H" may be added to the sub-region abbreviation (e.g., "FRL1" indicates framework sub-region 1 of the light chain variable region). Unless specified, the numbering of framework residues is according to Kabat. It is noted that, in certain embodiments, the HCV core protein-binding molecules of the present invention may have less than a complete framework (e.g. the HCV core protein binding molecule may have a portion of a framework that only contains one or more of the four sub-regions).

As used herein, the term "fully human framework" refers to an antibody framework with an amino acid sequence ordinarily found in humans. Examples of fully human frameworks, include, but are not limited to, KOL, NEWM, REI, EU, TUR, TEI, LAY and POM (See, e.g., Kabat et al., (1991) Sequences of Proteins of Immunological Interest, US Department of Health and Human Services, NIH, USA; and Wu et al., (1970) J. Exp. Med. 132, 211-250, both of which are herein incorporated by reference).

As used herein, the terms "subject" and "patient" refer to a mammal.

As used herein, the terms "an oligonucleotide having a nucleotide sequence encoding a polypeptide," "polynucleotide having a nucleotide sequence encoding a polypeptide," and "nucleic acid sequence encoding a peptide" means a nucleotide sequence comprising the coding region of a particular polypeptide. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

As used herein, the term "the complement of" a given sequence is used in reference to the sequence that is completely complementary to the sequence over its entire length. For example, the sequence 5'-A-G-T-A-3' is "the complement" of the sequence 3'-T-C-A-T-5'. The present invention also provides the complement of the sequences described herein (e.g., the complement of the nucleic acid sequences in SEQ ID NOS: 9 and 10, and truncated versions thereof).

The term "isolated" when used in relation to a nucleic acid, as in "an isolated oligonucleotide" or "isolated polynucleotide" or "isolated nucleic acid sequence encoding an HCV core protein binding molecule" (see, e.g., FIG. 8) refers to a nucleic acid sequence that is identified and separated from at least one contaminant nucleic acid with which it is ordinarily associated (e.g. host cell proteins).

As used herein, the term "purified" or "to purify" refers to the removal of contaminants from a sample. For example, HCV core protein-binding molecules (e.g., antibodies or antibody fragments) may be purified by removal of contaminating non-immunoglobulin proteins; they are also purified by the removal of immunoglobulins that do not bind to the same antigen. The removal of non-immunoglobulin proteins and/or the removal of immunoglobulins that do not bind the particular antigen results in an increase in the percentage of antigen specific immunoglobulins in the sample. In another example, recombinant antigen-specific polypeptides are expressed in bacterial host cells and the polypeptides are purified by the removal of host cell proteins; the percentage of recombinant antigen-specific polypeptides is thereby increased in the sample.

As used herein, the term "Fc region" refers to a C-terminal region of an immunoglobulin heavy chain. The "Fc region" may be a native sequence Fc region or a variant Fc region (e.g., with increased or decreased effector functions).

The terms "affinity," "binding affinity" and "$K_d$" refer to the equilibrium dissociation constant (expressed in units of concentration) associated with each HCV core protein binding molecule—HCV core protein complex. The binding affinity is directly related to the ratio of the off-rate constant (generally reported in units of inverse time, e.g., seconds') to the on-rate constant (generally reported in units of concentration per unit time, e.g., molar/second). The binding affinity may be determined by, for example, an ELISA assay, kinetic exclusion assay or surface plasmon resonance. It is noted that certain epitopes can occur repetitively (multivalent) on a cell surface and that the dissociation constant ($k_{off}$) for the binding of an antibody to a repetitive epitope may be greatly diminished over the dissociation constant for the reaction of the same antibody with the corresponding ligand in univalent form. The diminished dissociation constant arises because when one antibody-ligand bond dissociates, other bonds hold the bivalent (or multivalent) antibody to the multivalent ligand, allowing the dissociated bond to form again. The dissociation constant for the reaction between bivalent (or multivalent) Ab and multivalent ligand has been termed the functional affinity to contrast it with intrinsic affinity, which is the association constant for an antibodies representative individual site.

The terms "dissociation", "dissociation rate" and "$k_{off}$" as used herein, are intended to refer to the off rate constant for dissociation of a HCV core protein binding molecule from the antibody/antigen complex.

The terms "association", "association rate" and "$k_{on}$" as used herein, are intended to refer to the on rate constant for association of a HCV core protein binding molecule with an antigen to form an antibody/antigen complex.

The terms "effective concentration" and "$EC_{50}$" as used herein, are intended to refer to the concentration of a HCV core protein binding molecule capable of interacting with sufficient quantities of HCV core protein molecules to produce an effect on approximately 50% of the treated cells.

The present invention relates to HCV core and minicore-binding molecules and nucleic acid sequences encoding such molecules. In particular embodiments, the present invention provides HCV core and minicore-binding molecules (e.g., monoclonal antibodies or antibody fragments) with particular light chain and/or heavy chain CDRs (e.g., selected from SEQ ID NOS:2-4 and 6-8) and methods for using such molecules to detect the presence of HCV core proteins (e.g., mature p21 core protein or minicore proteins) in a sample.

In certain embodiments, the HCV core protein-binding proteins comprise one or more of the CDRs shown in SEQ ID NOS: 2-4 and 6-8, and/or CDRs with one or more conservative or non-conservative amino acid changes in these SEQ ID NOS. Also provided are nucleic acid sequences substantially similar to SEQ ID NOS: 9 and 10 (e.g., sequences with at least 80 . . . 90 . . . or 99% sequence identity). Changes to the amino acid sequences of the CDRs may be generated by changing the nucleic acid sequence encoding the amino acid sequence. A nucleic acid sequence encoding a variant of a given CDR may be prepared by methods known in the art using the guidance of the present specification for particular sequences. These methods include, but are not limited to, preparation by site-directed (or oligonucleotide-mediated) mutagenesis, PCR mutagenesis, and cassette mutagenesis of an earlier prepared nucleic acid encoding the CDR.

Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting CDR (see, e.g., Vallette et. al., (1989) Nucleic Acids Res. 17: 723-733, hereby incorporated by reference). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., (1985) Gene 34: 315-323, hereby incorporated by reference. The starting material is the plasmid (or other vector) comprising the starting CDR DNA to be mutated. The codon(s) in the starting DNA to be mutated are identified. There should be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a CDR variant can be determined, and a nucleic acid sequence encoding such amino acid sequence variant can be generated synthetically. Conservative modifications in the amino acid sequences of the CDRs may also be made. Naturally occurring residues are divided into classes based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and (6) aromatic: trp, tyr, phe.

Conservative substitutions will entail exchanging a member of one of these classes for another member of the same class in a particular CDR, such as in SEQ ID NOS:2-4 and 6-8. The present invention also provides the complement of the nucleic acid sequences shown SEQ ID NOS: 9 and 10, as well as nucleic acid sequences that will hybridize to these nucleic acid sequences under low, medium, and high stringency conditions.

The CDRs of the present invention may be employed with any type of framework. The framework shown in FIG. 7 is the original mouse framework from the Neo4 antibody. The CDRs may be used with other murine frameworks, which are known in the art. In other embodiments, the CDRs are used with fully human frameworks, or framework subregions. For example, the NCBI web site contains the sequences for known human framework regions. Examples of human VH sequences include, but are not limited to, VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81, which are provided in Matsuda et al., (1998) J. Exp. Med. 188:1973-1975, that includes the complete nucleotide sequence of the human immunoglobulin chain variable region locus, herein incorporated by reference. Examples of human VK sequences include, but are not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8, which are provided in Kawasaki et al., (2001) Eur. J. Immunol. 31:1017-1028; Schable and Zachau, (1993) Biol. Chem. Hoppe Seyler 374:1001-1022; and Brensing-Kuppers et al., (1997) Gene 191:173-181, all of which are herein incorporated by reference. Examples of human VL sequences include, but are not limited to, V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6, which are provided in Kawasaki et al., (1997) Genome Res. 7:250-261, herein incorporated by reference. Fully human frameworks can be selected from any of these functional germline genes. Generally, these frameworks differ from each other by a limited number of amino acid changes. These frameworks may be used with the CDRs described herein. Additional examples of human frameworks which may be used with the CDRs of the present invention include, but are not limited to, KOL, NEWM, REI, EU, TUR, TEI, LAY and POM (See, e.g., Kabat et al., (1991) Sequences of Proteins of Immunological Interest, US Department of Health and Human Services, NIH, USA; and Wu et al., (1970), J. Exp. Med. 132:211-250, both of which are herein incorporated by reference).

In certain embodiments, the HCV core protein-binding molecules of the present invention comprise antibodies or antibody fragments (e.g., comprising one or more of the CDRs described herein). An antibody, or antibody fragment, of the present invention can be prepared, for example, by recombinant expression of immunoglobulin light and heavy chain genes in a host cell. For example, to express an antibody recombinantly, a host cell may be transfected with one or more recombinant expression vectors carrying DNA fragments encoding the immunoglobulin light and heavy chains of the antibody such that the light and heavy chains are expressed in the host cell and, preferably, secreted into the medium in which the host cell is cultured, from which medium the antibody can be recovered. Standard recombinant DNA methodologies may be used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al., all of which are herein incorporated by reference.

To express an antibody with one or more of the CDRs of the present invention, DNA fragments encoding the light and heavy chain variable regions are first obtained. These DNAs can be obtained by amplification and modification of germline light and heavy chain variable sequences using the polymerase chain reaction (PCR).

Once the germline VH and VL fragments are obtained, these sequences can be mutated to encode one or more of the CDR amino acid sequences disclosed herein (see, e.g., SEQ ID NOS:2-4 and 6-8). The amino acid sequences encoded by the germline VH and VL DNA sequences may be compared to the CDRs sequence(s) desired to identify amino acid residues that differ from the germline sequences. Then the appropriate nucleotides of the germline DNA sequences are mutated such that the mutated germline sequence encodes the selected CDRs (e.g., the six CDRs shown in FIG. 7), using the genetic code to determine which nucleotide changes should be made. Mutagenesis of the germline sequences may be carried out by standard methods, such as PCR-mediated mutagenesis (in which the mutated nucleotides are incorporated into the PCR primers such that the PCR product contains the mutations) or site-directed mutagenesis. In other embodiments, the variable region is synthesized de novo (e.g., using a nucleic acid synthesizer).

Once DNA fragments encoding the desired VH and VL segments are obtained (e.g., by amplification and mutagenesis of germline VH and VL genes, or synthetic synthesis, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operably linked to another DNA fragment encoding another polypeptide, such as an antibody constant region or a flexible linker. The isolated DNA encoding the VH region can be converted to a full-length heavy chain gene by operably linking the VH-encoding DNA to another DNA molecule encoding heavy chain constant regions (CH1, CH2 and CH3). The sequences of mouse and human heavy chain constant region genes are known in the art and DNA fragments encompassing these regions can be obtained by standard PCR amplification. The heavy chain constant region can be, for example, an IgG1, IgG2, IgG3, IgG4, IgA, IgE, IgM or IgD constant region. For a Fab fragment heavy chain gene, the VH-encoding DNA can be operably linked to another DNA molecule encoding only the heavy chain CH1 constant region.

The isolated DNA encoding the VL region can be converted to a full-length light chain gene (as well as a Fab light chain gene) by operably linking the VL-encoding DNA to another DNA molecule encoding the light chain constant region, CL. The sequences of mouse and human light chain constant region genes are known in the art (see e.g., Kabat, E. A., et al., (1991) Sequences of Proteins of immunological Interest, Fifth Edition, U.S. Department of Health and Human Services. NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments may be operably linked to another fragment encoding a flexible linker, e.g., encoding the amino acid sequence (Gly4-Ser)$_3$, such that the VH and VL sequences can be expressed as a contiguous single-chain protein, with the VL and VH regions joined by the flexible linker (see e.g., Huston et al., (1988) Proc. Natl. Acad. Sci. USA 85:5879-5883; and McCafferty et al., (1990) Nature 348:552-554), all of which are herein incorporated by reference).

To express the antibodies, or antibody fragments of the invention, DNAs encoding partial or full-length light and heavy chains, (e.g. obtained as described above), may be inserted into expression vectors such that the genes are operably linked to transcriptional and translational control sequences. In this context, the term "operably linked" is intended to mean that an antibody gene is ligated into a vector such that transcriptional and translational control sequences within the vector serve their intended function of regulating the transcription and translation of the antibody gene. The expression vector and expression control sequences are generally chosen to be compatible with the expression host cell used. The antibody light chain gene and the antibody heavy chain gene can be inserted into separate vectors or, more typically, both genes are inserted into the same expression vector. The antibody genes may be inserted into the expression vector by standard methods (e.g., ligation of complementary restriction sites on the antibody gene fragment and vector, or blunt end ligation if no restriction sites are present). Prior to insertion of the light or heavy chain sequences, the expression vector may already carry antibody constant region sequences. For example, one approach to converting the VH and VL sequences to full-length antibody genes is to insert them into expression vectors already encoding heavy chain constant and light chain constant regions, respectively, such that the VH segment is operably linked to the CH segment(s) within the vector and the VL segment is operably linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990), herein incorporated by reference. It will be appreciated by those skilled in the art that the design of the expression vector, including the selection of regulatory sequences may depend on such factors as the choice of the host cell to be transformed, the level of expression of protein desired, etc. In certain embodiments, regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma virus. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al., all of which are herein incorporated by reference.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634.665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neomycin gene (for G418 selection).

For expression of the light and heavy chains, the expression vector(s) encoding the heavy and light chains may be transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like.

In certain embodiments, the expression vector used to express the HCV core protein-binding molecules of the present invention are viral vectors, such as retro-viral vectors. Such viral vectors may be employed to generate stably transduced cell lines (e.g. for a continued source of the HCV core protein binding molecules). In some embodiments, the GPEX gene product expression technology (from Gala Design, Inc., Middleton, Wis.) is employed to generate HCV core protein-binding molecules (and stable cell lines expressing the HCV core protein binding molecules). In particular embodiments, the expression technology described in WO0202783 and WO0202738 to Bleck et al. (both of which are herein incorporated by reference in their entireties) is employed.

Mammalian host cells for expressing the recombinant antibodies of the invention include PER.C6™ cells (Crucell, The Netherlands), Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In other embodiments, the host cells express GnT III as described in WO9954342 and U.S. Pat. Pub. 20030003097, both herein incorporated by reference, such that expressed HCV core protein-binding molecules have increased ADCC activity. When recombinant expression vectors encoding antibody genes are introduced into mammalian host cells, the antibodies are generally produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain of an antibody of this invention.

Recombinant DNA technology may also be used to remove some or all of the DNA encoding either or both of the light and heavy chains that is not necessary for binding to HCV core proteins. The molecules expressed from such truncated DNA molecules are also encompassed by the antibodies of the invention. In addition, bi-functional antibodies may be produced in which one heavy and one light chain are an antibody of the invention and the other heavy and light chain are specific for an antigen other than an HCV core protein (e.g., by crosslinking an antibody of the invention to a second antibody by standard chemical crosslinking methods).

In certain embodiments, the antibodies and antibody fragments of the present invention are produced in transgenic animals. For example, transgenic sheep and cows may be engineered to produce the antibodies or antibody fragments in their milk (see, e.g., Pollock D P, et al., (1999) Transgenic milk as a method for the production of recombinant antibodies. J. Immunol. Methods 231:147-157, herein incorporated by reference). The antibodies and antibody fragments of the present invention may also be produced in plants (see, e.g., Larrick et al., (2001) Production of secretory IgA antibodies in plants. Biomol. Eng. 18:87-94, herein incorporated by reference). Additional methodologies and purification protocols are provided in Humphreys et al., (2001) Therapeutic antibody production technologies: molecules applications, expression and purification, Curr. Opin. Drug Discov. Devel. 4:172-185, herein incorporated by reference. In certain embodiments, the antibodies or antibody fragments of the present invention are produced by transgenic chickens (see, e.g., US Pat. Pub. Nos. 20020108132 and 20020028488, both of which are herein incorporated by reference).

In certain embodiments, the HCV core protein-binding molecules of the present invention (e.g., as antibodies or antibody fragments) are useful for immunoassays which detect or quantify HCV core proteins (mature core or minicore proteins) in a sample (e.g., a purified blood sample from a subject suspected of being infected with HCV). In some embodiments, an immunoassay for HCV core proteins typically comprises incubating a biological sample in the presence of a detectably labeled antibody or antibody fragment of the present invention capable of selectively binding to HCV core or minicore, and detecting the labeled peptide or antibody which is bound in a sample. Various clinical assay procedures are well known in the art.

The present disclosure provides immunoassay methods for determining the presence, amount or concentration of HCV core protein in a test sample. Any suitable assay known in the art can be used in such a method. Examples of such assays include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), an ARCHITECT assay (ABBOTT), a bioluminescence resonance energy transfer (BRET), and homogeneous chemiluminescent assay, etc.

An HCV core protein binding molecule can be captured on beads or nitrocellulose, or on any other solid support which is capable of immobilizing soluble proteins (e.g., magnetic beads). A HCV core protein containing sample is then added to the support which is subsequently washed with suitable buffers to remove unbound proteins. A second, detectably labeled, molecule (e.g., antibody or peptide) that can bind to the HCV core protein binding molecule is added to the solid phase support that can then be washed with the buffer a second time to remove unbound molecules. The amount of bound label on the solid support can then be detected by known methods.

By "solid phase support" or "carrier" is intended any support capable of binding peptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble. The support material can have virtually any possible structural configuration so long as the coupled molecule retains its ability to bind to HCV core protein. Thus, the support configuration can be spherical, as in a bead, or cylindrical, as in the inside surface of a test tube, or the external surface of a rod. Alternatively, the surface can be flat such as a sheet, culture dish, test strip, microtiter plates, polystyrene beads, etc. Those skilled in the art will know many other suitable carriers for binding antibody, peptide or antigen, or can ascertain the same by routine experimentation.

Detectably labeling a HCV core protein binding molecule can be accomplished by coupling to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the HCV core protein-binding molecules of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the HCV core protein binding molecules, it is possible to detect HCV core proteins through the use of a radioimmunoassay (MA) (see, for example, Work, et al., (1978) Laboratory Techniques and Biochemistry in Molecular Biology, North Holland Publishing Company, N.Y.). The radioactive isotope can be detected by such means as the use of a gamma counter or a scintillation counter or by autoradiography.

It is also possible to label the HCV core protein-binding molecules with a fluorescent compound. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The HCV core protein-binding molecules can also be detectably labeled using fluorescence-emitting metals such as $^{125}$Eu, or others of the lanthanide series. These metals can be attached to the HCV core protein binding molecule using such metal chelating groups as diethylenetriaminepentaacetic acid (DTPA) or ethylenediamine-tetraacetic acid (EDTA).

The HCV core protein-binding molecules also can be detectably labeled by coupling to a chemiluminescent compound. The presence of the chemiluminescently labeled molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the HCV core protein-binding molecules of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the HCV core protein-binding molecules can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate to similarly prepared standards.

In some embodiments of the present invention, the HCV core protein (e.g., mature core or minicore) which is detected by the above assays can be present in a biological sample. Any sample containing HCV core proteins can be used. Preferably, the sample is a biological fluid such as, for example, blood, serum, lymph, urine, cerebrospinal fluid, amniotic fluid, synovial fluid, a tissue extract or homogenate, and the like. However, the invention is not limited to assays using only these samples, as it is possible for one of ordinary skill in the art to determine suitable conditions which allow the use of other samples.

In situ detection can be accomplished by removing a histological specimen from a patient, and providing the combination of labeled HCV core protein-binding molecules of the present invention to such a specimen. The HCV core protein binding molecule is preferably provided by applying or by overlaying the labeled HCV core protein binding molecule to a biological sample. Through the use of such a procedure, it is possible to determine not only the presence of HCV core proteins, but also the distribution of HCV core protein in the examined tissue.

In particular embodiments, the HCV core protein-binding molecules described herein are contemplated for use as immunodiagnostic reagents in combination immunoassays designed for the detection of multiple HCV components found in a test sample suspected of having been infected with HCV. Such assays can not only detect HCV core proteins, but also other regions of HCV, such as the NS3 region of HCV, the NS4 region of HCV, the NS5 region of HCV, or combinations thereof. One may employ, for example, capture antibodies or capture antigens to detect other regions of HCV. For purposes of capture, the antigens and/or antibodies of which the immunodiagnostic reagent is comprised can be coated on a solid support such as for example, a microparticle, (e.g., magnetic particle), bead, test tube, microtiter plate, cuvette, membrane, scaffolding molecule, film, filter paper, disc or chip. In this regard, where the immunodiagnostic reagent comprises a combination of antigens (e.g., directed at different HCV proteins or different fragments of the same HCV protein), the antigens can be co-coated on the same solid support or can be on separate solid supports. Likewise, where the immunodiagnostic reagent comprises one or more antibodies that will be used to capture one or more antigens from the test sample, such antibodies can be co-coated on the same solid support or can be on separate solid supports.

In certain embodiments, provided here are kits for the detection of HCV core proteins that include an HCV core protein detection molecule. Such kits may include any of the immunodiagnostic reagents described herein and may further include instructions for the use of the immunodiagnostic reagents in immunoassays for determining the presence of HCV in a test sample. The instructions can be in paper form or computer-readable form, such as a disk, CD, DVD, or the like. Alternatively or additionally, the kit can comprise a calibrator or control, e.g., purified, and optionally lyophilized, anti-HCV antibody or antigen, and/or at least one container (e.g., tube, microtiter plates or strips, which can be already coated with one or more of the capture components (antigens and/or antibodies) of the combination immunoassay) for conducting the assay, and/or a buffer, such as an assay buffer or a wash buffer, either one of which can be provided as a concentrated solution, a substrate solution for the detectable label (e.g., an enzymatic label), or a stop solution. In certain embodiments, the kit comprises all components, such as reagents, standards, buffers, diluents, etc., which are necessary to perform the assay. In specific embodiments, all the components are individually presented in the kit such that the immunoassay may be performed as a capture-on-the-fly type immunoassay in which the solid support is coated with an agent (e.g., avidin) that allows binding of the capturing moiety (e.g., a biotinylated anti-HCV core antibody as described herein) and the kit further comprises each of the individual capture and detection antigen pairs and the biotinylated capture antibodies in one container and a second container provides the detection antibody conjugate. The instructions for conducting the assay also can include instructions for generating a standard curve or a reference standard for purposes of quantifying anti-HCV antibody. The antibodies, calibrators and/or controls can be provided in separate containers or pre-dispensed into an appropriate assay format, for example, into microtiter plates. In one embodiment, there are two containers provided. In certain embodiments, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kits may also include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit may be provided in suitable containers as necessary, e.g., a microtiter plate. The kit can further include containers for holding or storing a sample (e.g., a container or cartridge for a sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

In certain embodiments, the detectable label is at least one acridinium compound. In such embodiments, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. It should be understood that in the immunodiagnostic reagent the antigens for antibody detection may be detectably labeled, and any antibodies provided in kit for use along with such reagents also may be detectably labeled. In certain embodiments, the kit can contain a solid support phase, such as a magnetic particle, bead, test tube, microtiter plate, cuvette, membrane, scaffolding molecule, film, filter paper, disc or chip.

EXAMPLES

The following examples are provided in order to demonstrate and further illustrate certain embodiments and aspects and are not to be construed as limiting the scope thereof.

Example 1

Generating the Neo4 Antibody

Figure 2:
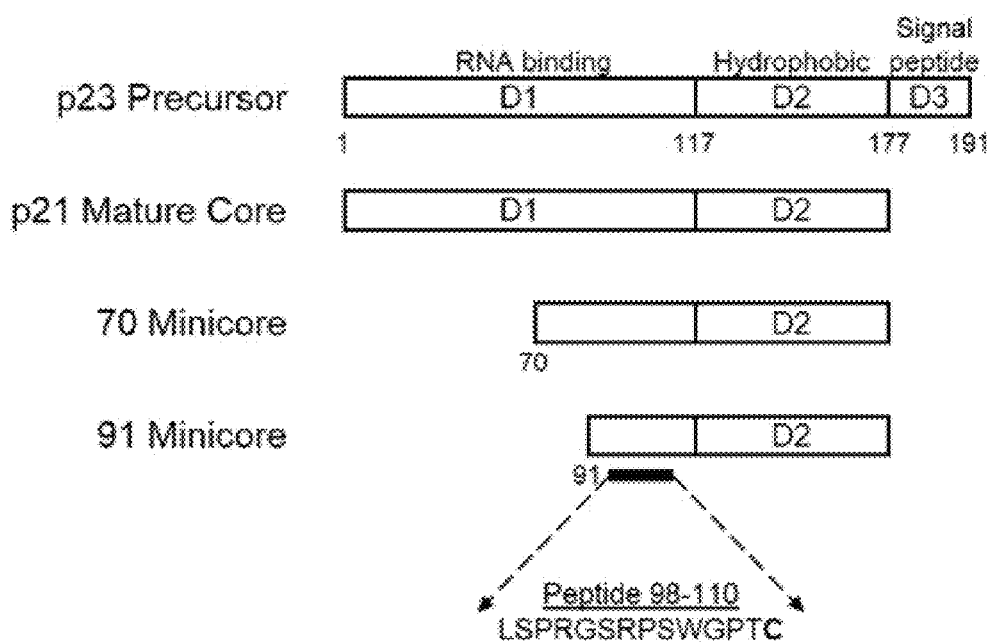
FIG. 2 shows the core proteins encoded by HCV, including the precursor p23, mature core p21, and N-terminally deleted 70 and 91 minicores. Both p21 mature core and minicore proteins contain the hydrophobic domain D2 which interacts with lipids. Minicores contain only part of domain D1, the RNA-binding domain. The location of the immunogen used in Example 1 (peptides 98-110; SEQ ID NO:35) with respect to full length HCV core and minicores 70 and 91 is shown in this figure.

This example describes generating the Neo4 mouse monoclonal antibody, which is able to detect HCV core and minicore proteins. Six peptides corresponding to HCV core amino acids 98-110, 104-113, 104-121, 110-124, 101-112 and 153-156 were used for immunization. The location of the peptide corresponding to amino acids 98-110 of HCV (LSPRGSRPSWGPT; SEQ ID NO: 35) core with respect to full length HCV core and minicores 70 and 91 is shown in FIG. 2.

Production of a Mouse Monoclonal Antibody Capable of Detecting Minicores with High Sensitivity.

Six synthetic peptides from the HCV core region (genotype 1b) were generated. The HCV core amino acid (aa) positions covered by each peptide are as follows: peptide 1, 98-110; peptide 2, 104-113; peptide 3, 104-121; peptide 4, 110-124; peptide 5, 101-112, and peptide 6, 153-165. Balb/C mice were each immunized with a combination of 2 different peptides; peptides 1 with 6; peptides 2 with 3; peptides 4 with 5; and peptides 1 with 5. All of the peptides were conjugated to keyhole limpet hemocyanin (KLH) at their C-terminus through an added cysteine residue. Mice were boosted four times. Spleens were collected for 2 independent fusions using the PEG 1500 chemical method. The Myeloma fusion partner used was SP2/0. Subcloning began after fusion screening. 150 cells were plated onto a 96 well plate which usually nets about 1 cell per well. Three rounds of subcloning were performed. Media used for the growth of cells from stable clones was Iscove's Modified Dulbecco's Medium (IMDM) with 10% FBS. Supernatants were analyzed by ELISA using the above core peptides. Hybridoma supernatants and ascites generated from ELISA-positive clones were then screened by western blot for their ability to detect minicores. One hybridoma clone (Neo4) was identified that gave an exceptionally strong signal at detecting minicore and p21 core proteins. The isotype of this antibody was determined to be IgG1. Antibodies were subsequently purified with Protein G sepharose and used for the detection of minicores.

Study Population.

Hepatologists and other providers at the Icahn School of Medicine at Mount Sinai recruited patients with a HCV viral load of 10 million IU/mL or above. Written informed consent was obtained and up to 16 mL of blood were collected, and serum was prepared. The study was conducted in compliance with the Icahn School Blood was obtained from four patients with high-titer HCV and two non-infected volunteers. Data on age, sex, HCV genotype, viral load, and other medical conditions were extracted from medical records (Table 1). All four HCV-infected patients were male and had a HCV viral load over 20 million IU/mL. Patients with a high HCV viral load were selected for this study because they were expected to have relatively high blood levels of HCV proteins, enabling the development of methods for detection.

TABLE 1

Clinical characteristics of patients

| Patient ID | HCV Viral Load (IU/mL) | HCV Genotype | Age (years) | Sex | Other |
|---|---|---|---|---|---|
| P1 | $7.46 \times 10^7$ | 1b | 49 | M | HIV co-infected |
| P2 | $2.91 \times 10^7$ | 1b | 63 | M | 5 years post kidney transplant |
| P3 | $1.23 \times 10^7$ | 1a | 67 | M | — |
| P4 | $>1 \times 10^{8}$* | 1a | 60 | M | 1 year post liver transplant and B cell lymphoma |
| N1 | — | — | 55 | M | Healthy control |
| N2 | — | — | 65 | F | Healthy control |

*Value was above the upper limit of detection of the assay

Isolation and Characterization of Minicores and p21 Core in Blood.

Figure 3:
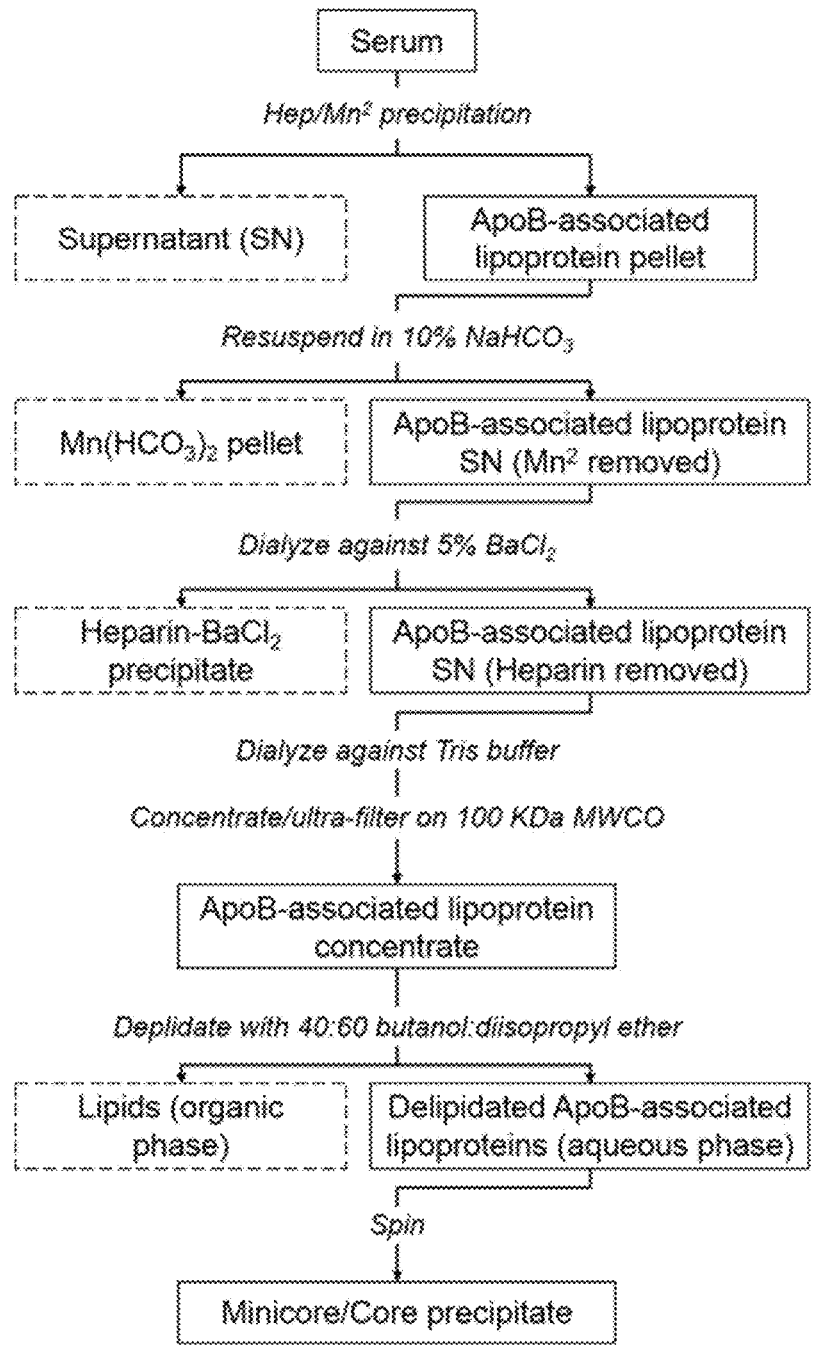
FIG. 3 shows a flow diagram of an exemplary purification scheme for isolating HCV core and HCV minicores.
Figure 4:
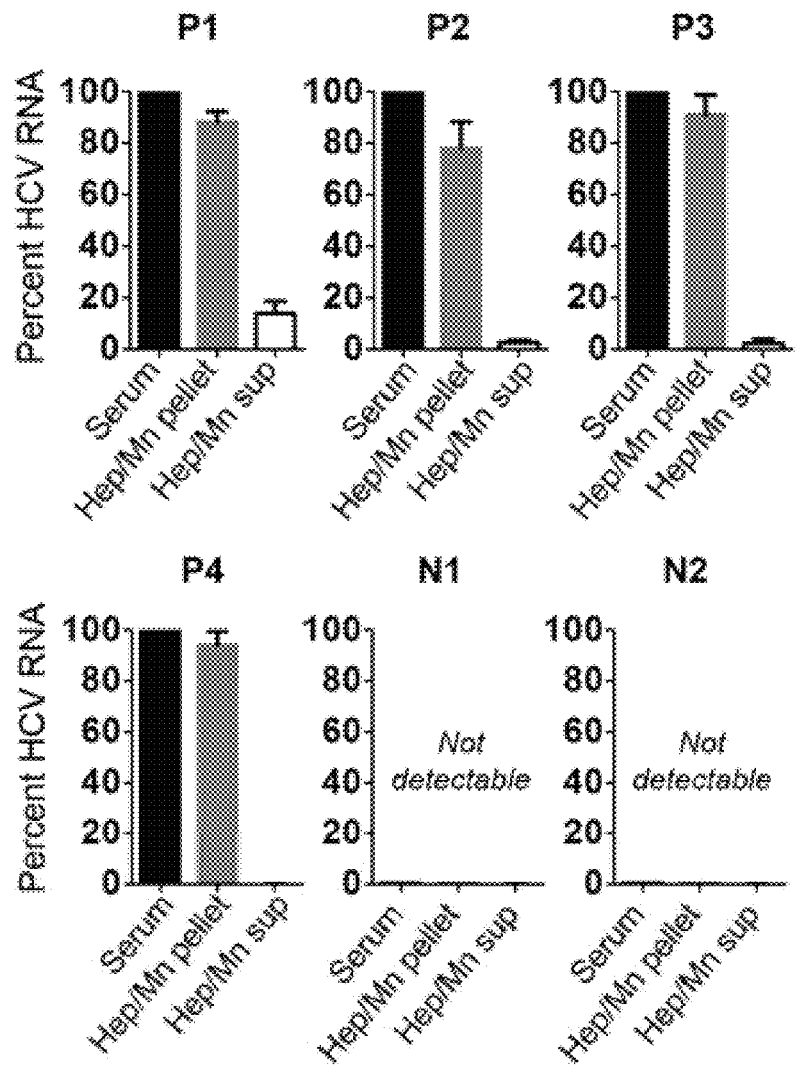
FIG. 4 shows results from Example 1 where it was shown that HCV RNA is enriched in the heparin/Mn$^{+2}$ pellet fraction in the four HCV patients (P1-P4), but not in two normal controls (N1-N2).

The general procedure for isolating minicore and mature p21 core protein from patient blood is shown in FIG. 3. An equal volume of 50 mM Tris (pH 7.3) and 150 mM NaCl was added to 3.5 mL of serum and passed through a 0.45 μm syringe filter to remove aggregates. ApoB-associated lipoproteins were then precipitated by mixing an equal volume of heparin/Mn$^{+2}$ solution containing 60 mM Tris (pH 7.3), 110 mM MnCl$_2$.4H$_2$O, 154 mM NaCl, and 400 USP/mL heparin. Solution was incubated for 1 h on ice in the dark. The precipitate was recovered by centrifugation at 3,000×g (30 min; 4° C.) and washed with gentle resuspension three times with 3.5 mL of an ice-cold solution containing 50 mM Tris (pH 7.3), 55 mM MnCl$_2$.4H$_2$0, 154 mM NaCl, and 200 USP units/mL heparin. Heparin/Mn$^{+2}$ was then removed: Manganese was removed from the heparin/Mn$^2$ pellet by resuspension in 2.0 or 2.5 mL of 10% NaHCO$_3$, which precipitates an insoluble Mn(HCO$_3$)$_2$ that is removed by centrifugation at 1,500×g (15 min; 4° C.). Heparin was removed by dialyzing 3 times (in 24 h) with one liter of 5% BaCl$_2$ in 20 mM Tris (pH 7) in a Slide-A-Lyzer Cassette G2 (Thermo Scientific) with a 20,000 MWCO. The supernatant was collected from the dialysis unit and the heparin-BaCl$_2$ insoluble complex was removed by centrifugation at 1,500×g (15 min; 4° C.). Excess BaCl$_2$ was removed from the supernatant by dialyzing 3 times (in 24 h; 4° C.) with one liter of THE buffer consisting of 20 mM Tris (pH 7.0), 0.15 M NaCl and 1 mM EDTA. The supernatant was collected from the dialysis unit and stored at −80° C. After thawing, the supernatant was concentrated using a 15 mL Amicon Ultra centrifugal filtration unit with a 100 kDa MWCO (Millipore) (3,200×g; 90 min; 4° C.). Concentrated volumes ranged between 130 μL and 210 μL. Finally, samples were delipidated to allow for loading onto a Western blot gel. Samples were delipidated using an extraction method previously described for whole serum and plasma which partitions proteins into an aqueous phase and lipids into an organic phase using a mixture of butanol and diisopropyl ether (butanol:DIPE at 40:60; v/v).[11] The original protocol was modified by using only a 1× volume of the 40:60 butanol:DIPE mixture to our sample rather than a 2× volume. It was found that the 2× volume can greatly dehydrate the aqueous phase. Also, instead of extracting by end-over-end tube rotation of the samples for 30 minutes, the samples were just briefly vortexed. The lipid-containing organic and protein-containing aqueous phases were separated by centrifugation at 400×g (2 min; 25° C.). The lower aqueous phase was immediately collected, placed on ice for 1 h, and then stored at −80° C. Incubation of the protein-containing aqueous phase on ice for 1 h followed by freeze-thawing led to the formation of a precipitate that was pelleted by gentle centrifugation at 1,000×g (30 sec; 4° C.). The pellet was solubilized in a solution containing 8 M Urea and 1% SDS, sonicated, adjusted with NuPage sample buffer, heated and loaded onto NuPAGE gels. This pellet contained core and minicore proteins. These proteins were not detected in the supernatant. After electrophoresis, gels were processed for western analysis. Protease inhibitors, Complete-EDTA free (Roche) and 1 mM phenylmethylsulfonyl fluoride (PMSF) were used throughout the purification procedure.

HCV-Infected Cell Culture Lysate.

Huh-7.5 cells infected with a Con1/JFH chimeric HCV were were lysed directly in culture dishes after three washes with Dulbecco's phosphate buffered saline with 2×LDS NuPage sample buffer (Life Technologies) containing 4% lithium dodecyl sulfate and 10% 2-mercaptoethanol.

Western Blot Analysis.

Samples were electrophoresed in 10% NuPAGE Bis-Tris gels (Life Technologies) and the proteins were transferred to 0.2 uM pore size, polyvinylidene difluoride (PVDF) membranes. Antibodies targeting the C-terminal portion of p21 core and used to detect minicores were a combination of Neo4 monoclonal antibody at a concentration of 2 ug/ml mixed with mAb 1 at 1 ug/ml, that we previously described.[1] Antibody targeting the N-terminal portion of core is mAb2 (Abbott Labs, epitope 32-36).

Quantification of HCV RNA.

QIAamp Viral RNA mini kit (Qiagen) was used to purify RNA from serum, Hep/Mn$^{+2}$ pellet and supernatant. For the heparin/Mn$^{+2}$ pellet and supernatatant, heparin was removed from the purified RNAs by treating with heparinase I (Sigma)[12]. Reverse transcription (RT) of RNA was performed using SuperScript III First-Strand Synthesis (Invitrogen) and random hexamers. RT-reaction products were then used for quantitative-PCR (q-PCR) using the LightCycler 480 SYBR Green I Master kit and the LightCycler 480 instrument (Roche).

Figure 5:
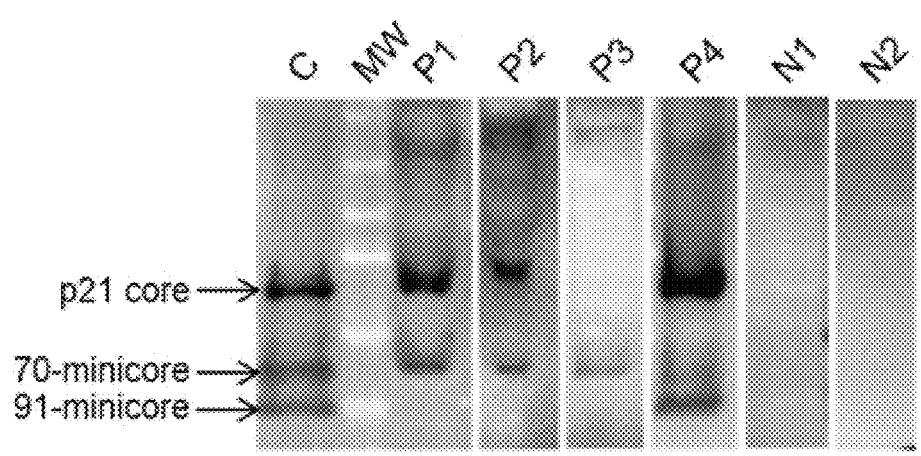
FIG. 5 shows results from Example 1, where minicores are detected by western blot in four HCV patients (lanes P1-P4) and not in two normal controls (lanes N1, N2). Cell culture supernatant of infected cells serves as a positive control (lane C).
Figure 6:
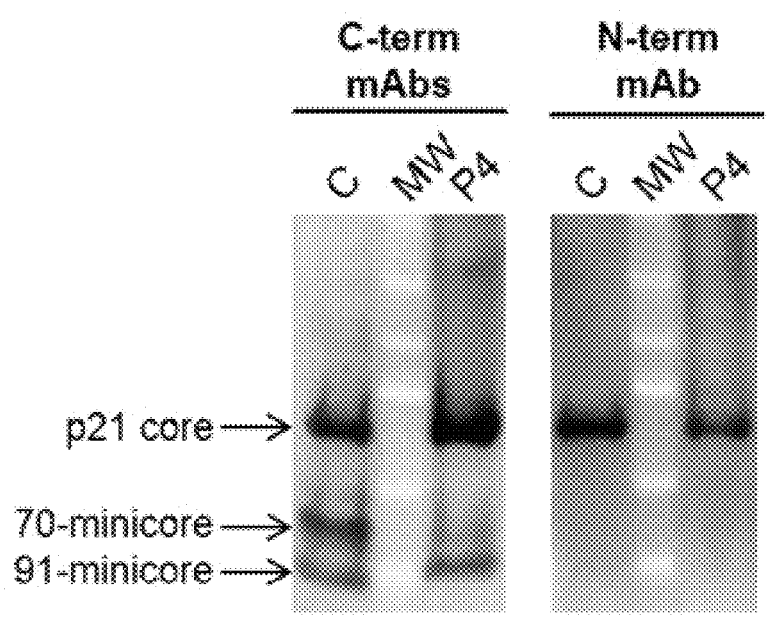
FIG. 6 shows results of Example 1, where duplicate Western blots of sample P4 were probed with antibodies directed either to the C-term or N-term portion of the core protein confirms the identity of minicores.

Minicores were present in the blood of all four patients (FIG. 5). The relative amounts of p21 core, 70 minicore and 91 minicore varied from patient to patient. Patient samples P1, P2, and P4 had prominent p21 core bands. Interestingly, P1, P2, and P4 were immune compromised as a result of HIV infection or immunosuppressive drugs, while P3 had no known immunological deficiency (Table 1). P1, P2, and P3 had prominent 70 minicore bands, and P4 had a prominent 91 minicore band. A cell culture lysate of HCV-infected Huh-7.5 cells provided molecular weight markers of the core protein isoforms (FIGS. 5 and 6, lanes C). To confirm the identity of the core isoform bands, duplicate Western blots of sample P4 were probed with antibodies specific for either the N- or the C-terminal portion of the core protein (FIG. 6), allowing detection of p21 core only (N-term) or p21 plus the 70 and 91 minicores (C-term).

This study provides direct evidence that HCV-expressed non-classical proteins (minicores) are present in blood during natural infections in addition to the conventional proteins. Minicores were detected in all four high HCV viral load patients. The presence of relatively large quantities of minicores in blood suggests that they enhance viral transmission and/or pathogenesis/persistence.

Example 2

Neo4 Antibody Sequencing

This example describes how the nucleotide and deduced amino acid sequences of the light and heavy chain variable domains of the Neo4 monoclonal antibody were determined. Total cellular RNA was extracted from the anti-HCV core Neo4 hybridoma cells using Trizol (TriZOL, Invitrogen) per manufacturer's recommendations. To sequence the variable domains, cDNA was generated from the extracted RNA using Superscript III (Life Technologies) and an oligo-dT primer (Novagen). Amplification of the respective immunoglobulin variable sequences was performed by 5'RACE PCR using a dC-anchor primer and a murine consensus heavy or light chain primer. Purified products were cloned into pCR™2.1-TOPO® (Life Technologies) which was then used to transform E. coli. For sequence analysis, variable heavy and variable light chain fragments from multiple E. coli colonies were PCR amplified using M13 forward and reverse primers. Sequencing was performed using the Big-Dye Terminator v3.1 cycle sequencing kit (Applied Biosystems) on the ABI 3130xl Genetic Analyzer. At least 5 heavy or light chain clones were viewed, analyzed, and annotated using Vector NTI Advance (Life Technologies) to create the consensus nucleotide sequences. FIG. 7 shows the amino acid sequence of the light chain variable region (FIG. 7A, SEQ ID NO: 1) and the heavy chain variable region (FIG. 7B, SEQ ID NO:5) of Neo4. The CDRs were identified by visual inspection of the deduced amino acid sequences relative to the locations of conserved features within the respective domains (see, Kabat et al., (1987) Sequences of Proteins of Immunological Interest, 4th ed., U. S. Govt. Printing Office No. 165-492, Bethesda, Md.). FIG. 7A shows the light chain CDRs underlined, which include CDRL1 (RASKSVNEYGYTYMH; SEQ ID NO: 2), CDRL2 (LASNLDS; SEQ ID NO:3), and CDRL3 (QHSRELPYT, SEQ ID NO:4). FIG. 7B shows the heavy chain CDRs underlined, which include CDRH1 (GFSITSSVYCWQ; SEQ ID NO: 6), CDRH2 (RICYDGSVDYSPSITS; SEQ ID NO: 7), and CDRH3 (ENHIDYYDTTYPSFDV; SEQ ID NO: 8). FIG. 8A shows the nucleic acid sequence encoding the light chain variable region of Neo4 (SEQ ID NO: 9), and FIG. 8B shows the nucleic acid sequence encoding the heavy chain variable region of Neo4 (SEQ ID NO: 10).

Example 3

Neo4 and C11-3 (ABT-4) Antibody Epitope Mapping

Purified Neo4 and C11-3 (ABT-4) monoclonal IgG samples were analyzed for reactivity to overlapping HCV core antigen peptides by EIA. Biotin-(SGSG)-15 mer HCV core-amide peptides were synthesized that overlapped by two amino acids and encompassed the entire length of HCV core protein amino acids 1-191 (Mimotopes). Each of the 89 synthesized peptides was coated in an individual micro-titer well as indicated on the peptide plate key (Table 2) as shown. The coated plates were kept dry in a sealed foil pouch and stored at <10 degrees C. until ready for use. A peptide coated plate for each test antibody was blocked using 3% BSA in PBS with 0.5% Tween 20. The blocked plates were washed with distilled water and a 2 ug/mL solution of purified IgG from each test sample diluted in BSA block solution was added to each peptide coated well of the blocked plate and allowed to incubate at room temperature for at least one hour. Following incubation the plates were washed with distilled water. A 200 ng/mL solution of peroxidase labeled F(ab')2 fragment goat anti-mouse IgG Fc fragment specific (Jackson Immunoresearch) in BSA block solution was added to all wells and incubated at room temperature for 30 minutes. The plates were washed with distilled water and o-phenylenediamine substrate was used as the chromagen to generate signal. Plates were read at 492 nm and the results were analyzed. Wells were considered positive if they had an EIA signal at least 3 times greater than background. The reactivity of ABT-4 to the peptides is shown with shading in Table 3, while the reactivity of the Neo4 antibody to the peptides is shown with shading in Table 4. As shown in these tables, the ABT-4 mAb reacts with peptide numbers 48-53 while the Neo4 reacts with peptide numbers 50-55.

TABLE 2

Peptide Plate Key

|   | 1 | 2  | 3  | 4  | 5  | 6  | 7  | 8  | 9  | 10 | 11 | 12    |
|---|---|----|----|----|----|----|----|----|----|----|----|-------|
| A | 1 | 9  | 17 | 25 | 33 | 41 | 49 | 57 | 65 | 73 | 81 | 89    |
| B | 2 | 10 | 18 | 26 | 34 | 42 | 50 | 58 | 66 | 74 | 82 | Blank |
| C | 3 | 11 | 19 | 27 | 35 | 43 | 51 | 59 | 67 | 75 | 83 | Blank |
| D | 4 | 12 | 20 | 28 | 36 | 44 | 52 | 60 | 68 | 76 | 84 | Blank |
| E | 5 | 13 | 21 | 29 | 37 | 45 | 53 | 61 | 69 | 77 | 85 | Blank |
| F | 6 | 14 | 22 | 30 | 38 | 46 | 54 | 62 | 70 | 78 | 86 | Blank |
| G | 7 | 15 | 23 | 31 | 39 | 47 | 55 | 63 | 71 | 79 | 87 | Blank |
| H | 8 | 16 | 24 | 32 | 40 | 48 | 56 | 64 | 72 | 80 | 88 | Blank |

TABLE 3

HCV ABT-4

|   | 1    | 2    | 3    | 4    | 5    | 6    | 7    | 8    | 9    | 10   | 11   | 12   |
|---|------|------|------|------|------|------|------|------|------|------|------|------|
| A | 0.05 | 0.06 | 0.07 | 0.06 | 0.07 | 0.07 | 0.97 | 0.07 | 0.07 | 0.07 | 0.07 | 0.07 |
| B | 0.06 | 0.06 | 0.06 | 0.06 | 0.06 | 0.07 | 0.97 | 0.07 | 0.07 | 0.07 | 0.07 | 0.07 |
| C | 0.06 | 0.07 | 0.06 | 0.06 | 0.06 | 0.06 | 1.00 | 0.07 | 0.07 | 0.07 | 0.07 | 0.07 |
| D | 0.06 | 0.07 | 0.06 | 0.06 | 0.06 | 0.07 | 0.96 | 0.07 | 0.06 | 0.06 | 0.06 | 0.06 |
| E | 0.05 | 0.06 | 0.06 | 0.06 | 0.06 | 0.07 | 0.36 | 0.06 | 0.06 | 0.06 | 0.06 | 0.06 |
| F | 0.07 | 0.06 | 0.06 | 0.06 | 0.06 | 0.07 | 0.08 | 0.06 | 0.06 | 0.06 | 0.06 | 0.06 |
| G | 0.06 | 0.06 | 0.06 | 0.06 | 0.06 | 0.07 | 0.06 | 0.06 | 0.06 | 0.06 | 0.07 | 0.06 |
| H | 0.06 | 0.06 | 0.07 | 0.07 | 0.08 | 0.81 | 0.07 | 0.07 | 0.08 | 0.07 | 0.09 | 0.07 |

TABLE 4

HCV Neo4

|   | 1    | 2    | 3    | 4    | 5    | 6    | 7    | 8    | 9    | 10   | 11   | 12   |
|---|------|------|------|------|------|------|------|------|------|------|------|------|
| A | 0.06 | 0.05 | 0.04 | 0.04 | 0.05 | 0.04 | 0.05 | 0.05 | 0.04 | 0.04 | 0.04 | 0.05 |
| B | 0.06 | 0.05 | 0.05 | 0.04 | 0.04 | 0.04 | 1.03 | 0.05 | 0.05 | 0.05 | 0.04 | 0.05 |
| C | 0.05 | 0.05 | 0.05 | 0.04 | 0.04 | 0.05 | 0.96 | 0.05 | 0.05 | 0.10 | 0.05 | 0.05 |
| D | 0.06 | 0.07 | 0.05 | 0.04 | 0.05 | 0.05 | 0.93 | 0.06 | 0.04 | 0.05 | 0.05 | 0.05 |
| E | 0.05 | 0.05 | 0.05 | 0.04 | 0.04 | 0.04 | 0.96 | 0.05 | 0.05 | 0.05 | 0.05 | 0.04 |
| F | 0.06 | 0.06 | 0.07 | 0.05 | 0.05 | 0.06 | 1.01 | 0.05 | 0.04 | 0.06 | 0.05 | 0.05 |
| G | 0.07 | 0.06 | 0.05 | 0.05 | 0.05 | 0.05 | 0.97 | 0.04 | 0.05 | 0.05 | 0.05 | 0.04 |
| H | 0.06 | 0.06 | 0.05 | 0.06 | 0.05 | 0.04 | 0.04 | 0.04 | 0.04 | 0.05 | 0.05 | 0.05 |

A summary of the peptide reactivity of ABT-4 (C11-3) and Neo4 is provided in Table 5 below.

TABLE 5

Peptide Reactivity Summary

| HCV Core Peptide # | HCV Pore Peptide Sequence | SEQ ID NO | HCV Pore Region | HCV Core monoclonal antibody ABT-4 OD (A492 nm) | HCV Core monoclonal antibody Neo4 OD (A492 nm) |
|---|---|---|---|---|---|
| 48 | SGSGGWLLSPRGSRPSWGP | 11 | aa 95-109  | 0.95 | 0.04 |
| 49 | SGSGLLSPRGSRPSWGPTD | 12 | aa 97-111  | 1.03 | 0.05 |
| 50 | SGSGSPRGSRPSWGPTDPR | 13 | aa 99-113  | 1.03 | 1.03 |
| 51 | SGSGRGSRPSWGPTDPRRR | 14 | aa 101-115 | 1.01 | 0.96 |
| 52 | SGSGSRPSWGPTDPRRRSR | 15 | aa 103-117 | 1.01 | 0.93 |
| 53 | SGSGPSWGPTDPRRRSRNL | 16 | aa 105-119 | 0.36 | 0.96 |
| 54 | SGSGWGPTDPRRRSRNLGK | 17 | aa 107-121 | 0.08 | 1.01 |
| 55 | SGSGPTDPRRRSRNLGKVI | 18 | aa 109-123 | 0.08 | 0.97 |

Shown in Table 6 below, are the reactive HCV core peptides aligned, with the minimal overlap shaded. For Abt-4, the reactive sequence is shown to span from amino acid 95 to amino acid 117 of the core peptide sequence, with the minimum reactive sequence spanning from amino acid 103 to amino acid 109. For Neo4, the reactive sequence is shown to span from amino acid 99 to amino acid 123 of the core peptide sequence, with the minimum reactive sequence spanning from amino acid 109 to amino acid 113.

TABLE 6

Abt4 (C11-3)

```
GWLLSPRGSRPSWGP      (SEQ ID NO: 19)
 LLSPRGSRPSWGPTD     (SEQ ID NO: 20)
    SPRGSRPSWGPTDPR  (SEQ ID NO: 21)
     RGSRPSWGPTDPRRR (SEQ ID NO: 22)
      SRPSWGPTDPRRRSR (SEQ ID NO: 23)
```

Neo4

Example 4

HCV Core Peptide Reactivity of Anti-Core Monoclonal Antibodies

Assay wells were coated with sheep anti-mouse IgG Fc specific antibody and incubated overnight. The coating solution was then removed; the wells blocked using BSA/tween in PBS and then washed with dH2O. Serially diluted antibody (in block) test samples (Neo4 antibody and Abt-4 antibody) were then added, the plates incubated for at least 1 hour and then washed. Next, biotin labeled peptides (diluted to 500 ng/mL in block) were added, the plates incubated for 10 minutes while shaking at 700 rpm and then washed. Peroxidase conjugated streptavidin (diluted to 200 ng/mL in block) was then added to all assay wells, incubated for 20 minutes while shaking at 700 rpm and then washed. Finally, color was developed using OPD and signal quenched using 1N $H_2SO_4$. Signal was read at 492 nm. Data are tabulated and summarized in Table 7 below.

TABLE 7

| | normal mouse serum sera dil (1:X) | | | | | | | | | | | |
|---|---|---|---|---|---|---|---|---|---|---|---|---|
| bt-pep | 500 | 1,000 | 2,000 | 4,000 | 8,000 | 16,000 | 32,000 | 64,000 | 128,000 | 256,000 | 512,000 | 1.1 MM |
| WT1STHV | 0.0625 | 0.0552 | 0.0511 | 0.053 | 0.0537 | 0.06 | 0.0635 | 0.0628 | 0.067 | 0.0675 | 0.0743 | 0.0585 |
| Mut1T110N | 0.2575 | 0.0516 | 0.0617 | 0.0501 | 0.057 | 0.0626 | 0.0667 | 0.0702 | 0.0651 | 0.0677 | 0.0759 | 0.0631 |
| Mut6T110S | 0.2025 | 0.0545 | 0.0531 | 0.0505 | 0.0523 | 0.0611 | 0.0591 | 0.0631 | 0.069 | 0.0674 | 0.065 | 0.0621 |
| C113WT | 0.0603 | 0.056 | 0.0534 | 0.0532 | 0.0589 | 0.0537 | 0.0644 | 0.0623 | 0.066 | 0.066 | 0.0708 | 0.0586 |
| C113T109N | 0.0619 | 0.051 | 0.0534 | 0.0536 | 0.0607 | 0.0714 | 0.0751 | 0.0674 | 0.068 | 0.0629 | 0.0931 | 0.0726 |
| 92-133 | 0.0636 | 0.0521 | 0.0603 | 0.0533 | 0.0756 | 0.1009 | 0.0822 | 0.0656 | 0.0668 | 0.0615 | 0.0715 | 0.0691 |
| blank | 0.0563 | 0.0488 | 0.0538 | 0.0486 | 0.0508 | 0.0549 | 0.0679 | 0.0596 | 0.0631 | 0.065 | 0.0772 | 0.0783 |
| blank | 0.0691 | 0.0503 | 0.048 | 0.0494 | 0.0543 | 0.0534 | 0.0694 | 0.0584 | 0.0622 | 0.0654 | 0.0637 | 0.0772 |
| bt-pep | 2000 | 1000 | 500 | 250 | 125 | 62.5 | 31.25 | 15.625 | 7.813 | 3.906 | 1.953 | 0.977 |
| | HCV C11-3 ng/mL Ab | | | | | | | | | | | |
| WT1STHV | 2.1334 | 2.0583 | 2.1436 | 1.8662 | 2.038 | 2.098 | 1.8905 | 1.5079 | 1.1164 | 0.6026 | 0.3531 | 0.1881 |
| Mut1T110N | 0.0915 | 0.0721 | 0.0765 | 0.0857 | 0.1268 | 0.1549 | 0.1066 | 0.1103 | 0.0966 | 0.079 | 0.0854 | 0.0755 |
| Mut6T110S | 1.7329 | 2.1499 | 2.237 | 1.8305 | 2.0224 | 2.1105 | 1.5367 | 0.8075 | 0.3435 | 0.2271 | 0.0964 | 0.1005 |
| C113WT | 1.821 | 2.3479 | 2.3525 | 1.8679 | 2.3715 | 2.1987 | 1.758 | 1.0506 | 0.6131 | 0.2717 | 0.1721 | 0.1029 |
| C113T109N | 0.0707 | 0.0806 | 0.0882 | 0.0963 | 0.1475 | 0.2015 | 0.1599 | 0.1161 | 0.1192 | 0.0833 | 0.1143 | 0.1041 |
| 92-133 | 1.4473 | 1.8692 | 1.9517 | 1.6777 | 1.8343 | 1.9204 | 1.5476 | 1.0138 | 0.5623 | 0.1832 | 0.1342 | 0.1163 |
| blank | 0.0657 | 0.071 | 0.0995 | 0.0639 | 0.0736 | 0.0987 | 0.1178 | 0.1047 | 0.101 | 0.0831 | 0.0937 | 0.0959 |
| blank | 0.0743 | 0.0711 | 0.0655 | 0.0644 | 0.0791 | 0.1032 | 0.1452 | 0.0979 | 0.1179 | 0.0856 | 0.0763 | 0.142 |
| | HCV Neo4 ng/mL Ab | | | | | | | | | | | |
| WT1STHV | 1.8978 | 2.0033 | 1.9126 | 1.9886 | 1.9279 | 1.8543 | 1.6701 | 1.4209 | 1.0414 | 0.6691 | 0.4092 | 0.2204 |
| Mut1T110N | 0.0882 | 0.0678 | 0.065 | 0.089 | 0.2042 | 0.1391 | 0.0938 | 0.0771 | 0.0729 | 0.0719 | 0.0728 | 0.0619 |
| Mut6T110S | 1.1667 | 1.165 | 1.1716 | 1.1549 | 1.2728 | 1.1072 | 0.4805 | 0.2502 | 0.1316 | 0.0847 | 0.0717 | 0.0644 |
| C113WT | 0.0766 | 0.2219 | 0.0561 | 0.0607 | 0.0599 | 0.0626 | 0.0622 | 0.0697 | 0.0731 | 0.0694 | 0.0765 | 0.0584 |
| C113T109N | 0.059 | 0.0591 | 0.0803 | 0.1105 | 0.0858 | 0.1106 | 0.0815 | 0.0736 | 0.0751 | 0.0717 | 0.0853 | 0.0784 |
| 92-133 | 1.3067 | 1.4138 | 1.4754 | 1.4019 | 1.3064 | 1.4726 | 1.1055 | 0.8058 | 0.45 | 0.2166 | 0.1293 | 0.0978 |
| blank | 0.0643 | 0.0581 | 0.0663 | 0.0538 | 0.0534 | 0.0641 | 0.0689 | 0.0674 | 0.0696 | 0.0728 | 0.093 | 0.0715 |
| blank | 0.0676 | 0.0515 | 0.051 | 0.0526 | 0.0512 | 0.0642 | 0.0723 | 0.0687 | 0.0708 | 0.0687 | 0.0715 | 0.0767 |

TABLE 6-continued

```
   SPRGSRPSWGPTDPR    (SEQ ID NO: 24)
    RGSRPSWGPTDPRRR   (SEQ ID NO: 25)
     SRPSWGPTDPRRRSR  (SEQ ID NO: 26)
      PSWGPTDPRRRSRNL (SEQ ID NO: 27)
       SGPTDPRRRSRNLGK (SEQ ID NO: 28)
         PTDPRRRSRNLGKVI (SEQ ID NO: 29)
```

Sequences of HCV core peptides are shown below where # denotes position 110 of the HCV core protein sequence.

```
                  #
WT1STHV   GSRPSWGPTDPRHRSRNVGKVID  (SEQ ID NO: 30)
MUT1T110N GSRPSWGPNDPRHRSRNVGKVID  (SEQ ID NO: 31)
```

-continued

| # | | |
|---|---|---|
| MUT6T110S | GSRPSWGPSDPRHRSRNVGKVID | (SEQ ID NO: 32) |
| C113WT | RGSRPSWGPTD | (SEQ ID NO: 33) |
| C113T110N | RGSRPSWGPND | (SEQ ID NO: 34) |

Differences in sequence relative to genotype 1 at position 110 are highlighted. Reactivity of C11-3 (Abt4) and Neo4 at the 15.6 ng/mL dilution are summarized below in Table 8.

TABLE 8

| bt-pep | HCV C11-3 15.6 ng/mL | HCV Neo4 15.6 ng/mL |
|---|---|---|
| WT1STHV | 1.5079 | 1.4209 |
| Mut1T110N | 0.1103 | 0.0771 |
| Mut6T110S | 0.8075 | 0.2502 |
| C113WT | 1.0506 | 0.0697 |
| C113T109N | 0.1161 | 0.0736 |
| 92-133 | 1.0138 | 0.8058 |
| blank | 0.1047 | 0.0674 |
| blank | 0.0979 | 0.0687 |

Both Neo4 and C11-3 (Abt-4) are sensitive to the T110N mutation common among non-genotype 1 and 2 isolates. However, Neo4 appears to more susceptible to the T110S mutation compared to Abt4. Neo4 does not bind to peptides terminating at position 111 indicating that the Neo4 epitope involves HCV core sequences downstream of position 111. This is consistent with the epitope mapping using the core peptide library wherein the Neo4 and Abt4 epitopes overlap but the Neo4 epitope is shifted downstream (C-terminally) relative to Abt 4 by about 3-4 amino acids.

Example 5

Neo4 Has Greater Sensitivity at Detecting p21 Core and 91 Minicore than Abt-4

Figure 9:
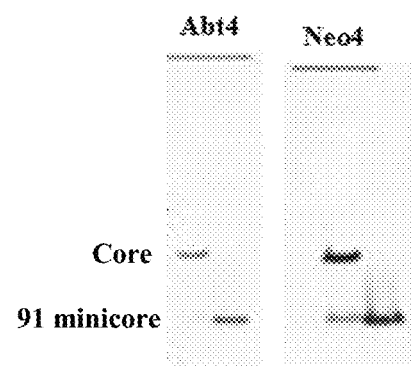
FIG. 9 shows the results of Example 5 in which Western blot analysis was used to compare the binding affinity of Neo4 and Abt-4 for p21 core and minicore proteins.

Core and 91-minicore proteins were expressed in 293T cells by transfecting plasmids which encode the respective proteins. The core and minicore plasmid constructs also contained the 5' two-thirds of the HCV E1 gene which normally follows the core gene in the HCV genome. Core protein sequences are cleaved away from E1 protein by cellular signal peptidase and signal peptide peptidase to yield the mature p21 core or minicore proteins. The 91-minicore construct begins with a start codon at codon 91 of the core gene. HCV sequences in both constructs were codon-optimized for enhanced expression. Cell extracts were prepared 48 hours post-transfection using a 2x lithium dodecyl sulfate (LDS) gel loading buffer followed by sonication. Extracts were diluted with 1x LDS loading buffer and were run on 10% Bis-Tris NuPage gels. Proteins were transferred to 0.2 uM pore size polyvinylidene difluoride (PVDF) membranes for Western blot analysis. The concentration of each antibody used in the Western blot analysis was at 2 µg/ml. The results are shown in FIG. 9, which shows that the Neo4 monoclonal antibody is better at detecting p21 core and 91-minicore proteins as compared to the Abt4 (CII-3) antibody.

REFERENCES

1. Eng F J, Walewski J L, Klepper A L, et al. Internal initiation stimulates production of p8 minicore, a member of a newly discovered family of hepatitis C virus core protein isoforms. J Virol 2009; 83:3104-14.
2. Akuta N, Suzuki F, Kawamura Y, et al. Amino acid substitutions in the hepatitis C virus core region are the important predictor of hepatocarcinogenesis. Hepatology 2007; 46:1357-64.
3. Akuta N, Suzuki F, Hirakawa M, et al. Amino acid substitutions in the hepatitis C virus core region of genotype 1b are the important predictor of severe insulin resistance in patients without cirrhosis and diabetes mellitus. J Med Virol 2009; 81:1032-9.
4. Akuta N, Suzuki F, Kawamura Y, et al. Predictive factors of early and sustained responses to peginterferon plus ribavirin combination therapy in Japanese patients infected with hepatitis C virus genotype 1b: Amino acid substitutions in the core region and low-density lipoprotein cholesterol levels. J Hepatol 2007; 46:403-10.
5. El-Shamy A E F, Doyle E, Andreo U, Klepper A, Muerhoff S, Schiano T, Dieterich D, Harty A I G, Perumalswami P, Rice C M and Branch A D Newly-Discovered HCV Minicores Circulate in Human Blood Hepatology 2014; 60: 1056A (Abstract #1782).
6. Nielsen S U, Bassendine M F, Burt A D, et al. Association between hepatitis C virus and very-low-density lipoprotein (VLDL)/LDL analyzed in iodixanol density gradients. J Virol 2006; 80:2418-28.
7. Andre P, Komurian-Pradel F, Deforges S, et al. Characterization of low- and very-low-density hepatitis C virus RNA-containing particles. J Virol 2002; 76:6919-28.
8. Nielsen S U, Bassendine M F, Burt A D, et al. Characterization of the genome and structural proteins of hepatitis C virus resolved from infected human liver. J Gen Virol 2004; 85:1497-507.
9. Goeser T, Muller H M, Ye J, et al. Characterization of antigenic determinants in the core antigen of the hepatitis C virus. Virology 1994; 205:462-9.
10. Ross R S, Viazov S, Salloum S, et al. Analytical performance characteristics and clinical utility of a novel assay for total hepatitis C virus core antigen quantification. J Clin Microbiol 2010; 48:1161-8.
11. Cham B E, Knowles B R. A solvent system for delipidation of plasma or serum without protein precipitation. J Lipid Res 1976; 17:176-81.
12. Johnson M L, Navanukraw C, Grazul-Bilska A T, et al. Heparinase treatment of RNA before quantitative real-time RT-PCR. Biotechniques 2003; 35:1140-2, 1144.

We claim:

1. A hepatitis C virus (HCV) core protein-binding molecule, comprising:
   a) a light chain variable region comprising
      i) a first light chain complementarity determining region (CDRL1) consisting of an amino acid sequence selected from the group consisting of SEQ ID NO: 2, and SEQ ID NO: 2 with one or more conservative amino acid changes;
      ii) a second light chain CDR (CDRL2) consisting of an amino acid sequence selected from the group consisting of SEQ ID NO:3 and SEQ ID NO:3 with one or more conservative amino acid changes; and
      iii) a third light chain CDR (CDRL3) consisting of an amino acid sequence selected from the group consisting of SEQ ID NO:4 and SEQ ID NO:4 with one or more conservative amino acid changes; and
   b) a heavy chain variable region, comprising
      i) a first heavy chain CDR (CDRH1) consisting of an amino acid sequence selected from the group consisting of SEQ ID NO:6 and SEQ ID NO:6 with one or more conservative amino acid changes;
      ii) a second heavy chain CDR (CDRH2) consisting of an amino acid sequence selected from the group consisting of SEQ ID NO:7 and SEQ ID NO:7 with one or more conservative amino acid changes; and
      iii) a third heavy chain CDR (CDRH3) consisting of an amino acid sequence selected from the group consisting of SEQ ID NO:8 and SEQ ID NO:8 with one or more conservative amino acid changes.

2. The HCV core protein-binding molecule of claim 1, wherein said HCV core protein-binding molecule is an antibody or antibody fragment capable of binding HCV p21 core protein and/or HCV 70 or 91 minicore protein.

3. The HCV core protein-binding molecule of claim 1, wherein said antibody fragment is an Fab or Fv antibody fragment.

4. The HCV core protein-binding molecule of claim 1, wherein said antibody fragment comprises an antigen binding portion of the Neo4 antibody.

5. The HCV core protein-binding molecule of claim 1, wherein said light and/or heavy chain variable region comprises a mouse or human framework region.

6. The HCV core protein-binding molecule of claim 1, wherein said HCV core protein-binding molecule has a higher binding affinity for p21 core or a minicore protein than monoclonal antibody C11-3 (ABT-4).

7. The HCV core protein-binding molecule of claim 1, wherein said HCV core protein-binding molecule is capable of binding HCV p21 core protein.

8. The HCV core protein-binding molecule of claim 1, wherein said HCV core protein-binding molecule is capable of binding HCV 70 or 91 minicore protein.

9. A composition comprising the HCV core protein-binding molecule of claim 1.

10. A nucleic acid comprising:
    a) a first nucleic acid sequence encoding a light chain variable region, wherein said light chain variable region comprises
       i) a CDRL1 consisting of an amino acid sequence selected from the group consisting of SEQ ID NO: 2 and SEQ ID NO: 2 with one or more conservative amino acid changes;
       ii) a CDRL2 consisting of an amino acid sequence selected from the group consisting of SEQ ID NO: 3 and SEQ ID NO: 3 with one or more conservative amino acid changes; and
       iii) a CDRL3 consisting of an amino acid sequence selected from the group consisting of SEQ ID NO: 4 and SEQ ID NO: 4 with one or more conservative amino acid changes; and
    b) a second nucleic acid sequence encoding a heavy chain variable region, wherein said heavy chain variable region comprises;
       i) a CDRH1 consisting of an amino acid sequence selected from the group consisting of SEQ ID NO:6 and SEQ ID NO:6 with one or more conservative amino acid changes;
       ii) a CDRH2 consisting of an amino acid sequence selected from the group consisting of SEQ ID NO:7 and SEQ ID NO:7 with one or more conservative amino acid changes; and
       iii) a CDRH3 consisting of an amino acid sequence selected from the group consisting of SEQ ID NO:8 and SEQ ID NO:8 with one or more conservative amino acid changes.

11. The nucleic acid of claim 10, wherein said light chain variable region comprises a mouse or human framework region.

12. The nucleic acid of claim 10, wherein said heavy chain variable region comprises a mouse or human framework region.

13. An expression vector comprising the nucleic acid of claim 10.

14. A host cell comprising a nucleic acid of claim 10.

15. A method of detecting an HCV core protein in a sample comprising:
    a) contacting a sample suspected of containing an HCV core protein with a HCV core protein-binding molecule of claim 1, wherein said HCV core protein binding molecule forms a complex with said HCV core protein if present in said sample; and
    b) detecting the presence or absence of said complex in said sample.

16. The method of claim 15, wherein said HCV core protein binding molecule comprises a detectable label.

17. The method of claim 15, wherein said HCV core protein comprises mature p21 core protein.

18. The method of claim 15, wherein said HCV core protein comprises 70 or 91 minicore protein.

19. The method of claim 15, further comprising contacting said sample with a conjugate molecule capable of binding to said HCV core protein binding molecule, wherein said conjugate molecule comprises a detectable label.

20. The method of claim 19, wherein said conjugate molecule comprises an anti-mouse antibody or a conjugate peptide.

21. The method of claim 15, wherein said HCV core protein binding molecule comprises biotin, and said method further comprises contacting said sample with streptavidin coated paramagnetic microparticles.

22. The method of claim 15, wherein said conjugate peptide comprises at least 5 consecutive amino acids from the amino acid sequence: SPRGSRPSWGPTDPRRRSRNLGKVI (SEQ ID NO: 36).

23. The method of claim 15, wherein said detecting comprises adding a chemiluminescent solution to said sample.

24. A host cell comprising an expression vector of claim 13.

* * * * *

SEQUENCE LISTING

<160> NUMBER OF SEQ ID NOS: 37

<210> SEQ ID NO 1
<211> LENGTH: 112
<212> TYPE: PRT
<213> ORGANISM: Artificial Sequence

```
<220> FEATURE:
<223> OTHER INFORMATION: synthetic peptide

<400> SEQUENCE: 1

Asp Ile Val Leu Thr Gln Ser Pro Ala Ser Leu Ile Val Ser Leu Gly
1               5                   10                  15

Gln Arg Ala Thr Ile Ser Cys Arg Ala Ser Lys Ser Val Asn Glu Tyr
            20                  25                  30

Gly Tyr Thr Tyr Met His Trp Tyr Gln Gln Lys Pro Gly Leu Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Gly Ile Lys Arg
            100                 105                 110

<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Arg Ala Ser Lys Ser Val Asn Glu Tyr Gly Tyr Thr Tyr Met His
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: synthetic peptide

<400> SEQUENCE: 3

Leu Ala Ser Asn Leu Asp Ser
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Gln His Ser Arg Glu Leu Pro Tyr Thr
1               5

<210> SEQ ID NO 5
<211> LENGTH: 126
<212> TYPE: PRT
<213> ORGANISM: Artificial Sequence
<220> FEATURE:
<223> OTHER INFORMATION: synthetic peptide

<400> SEQUENCE: 5

Gln Ile Gln Leu Lys Glu Ser Gly Pro Ala Val Ile Lys Pro Ser Gln
1               5                   10                  15

Ser Leu Ser Leu Thr Cys Ile Val Ser Gly Phe Ser Ile Thr Ser Ser
```

```
            20                  25                  30
Val Tyr Cys Trp Gln Trp Ile Arg Gln Pro Gly Lys Gly Leu Glu
        35                  40                  45

Trp Met Gly Arg Ile Cys Tyr Asp Gly Ser Val Asp Tyr Ser Pro Ser
    50                  55                  60

Ile Thr Ser Arg Gly Thr Ile Ser Arg Asp Thr Ser Leu Asn Lys Val
65                  70                  75                  80

Phe Phe Gln Leu Ser Ser Val Thr Asn Glu Asp Thr Ala Met Tyr Tyr
                85                  90                  95

Cys Ser Arg Glu Asn His Ile Asp Tyr Tyr Asp Thr Thr Tyr Pro Ser
            100                 105                 110

Phe Asp Val Trp Gly Ala Gly Thr Thr Val Thr Val Ser Ser
            115                 120                 125
```

<210> SEQ ID NO 6
<211> LENGTH: 12
<212> TYPE: PRT
<213> ORGANISM: Artificial Sequence
<220> FEATURE:
<223> OTHER INFORMATION: synthetic peptide

<400> SEQUENCE: 6

```
Gly Phe Ser Ile Thr Ser Ser Val Tyr Cys Trp Gln
1               5                   10
```

<210> SEQ ID NO 7
<211> LENGTH: 16
<212> TYPE: PRT
<213> ORGANISM: Artificial Sequence
<220> FEATURE:
<223> OTHER INFORMATION: synthetic peptide

<400> SEQUENCE: 7

```
Arg Ile Cys Tyr Asp Gly Ser Val Asp Tyr Ser Pro Ser Ile Thr Ser
1               5                   10                  15
```

<210> SEQ ID NO 8
<211> LENGTH: 16
<212> TYPE: PRT
<213> ORGANISM: Artificial Sequence
<220> FEATURE:
<223> OTHER INFORMATION: synthetic peptide

<400> SEQUENCE: 8

```
Glu Asn His Ile Asp Tyr Tyr Asp Thr Thr Tyr Pro Ser Phe Asp Val
1               5                   10                  15
```

<210> SEQ ID NO 9
<211> LENGTH: 336
<212> TYPE: DNA
<213> ORGANISM: Artificial Sequence
<220> FEATURE:
<223> OTHER INFORMATION: synthetic oligonucleotide

<400> SEQUENCE: 9

```
gacattgtgc tgacacagtc tcctgcttcc ttaattgtat ctctggggca gagggccacc      60
atctcgtgca gggccagcaa aagtgtcaat gaatatggct atacttatat gcactggtac     120
caacagaaac caggactgcc acccaaactc ctcatctatc ttgcatccaa tctagattct     180
ggggtccctg ccaggttcag tggcagtggg tctgggacag acttcaccct caacatccat     240
cctgtggagg aggaggatgc tgcaacctat tactgtcaac acagtaggga gcttccgtac     300
```

```
acgttcggag gggggaccaa gctggaaata aaacgg                                336
```

<210> SEQ ID NO 10
<211> LENGTH: 378
<212> TYPE: DNA
<213> ORGANISM: Artificial Sequence
<220> FEATURE:
<223> OTHER INFORMATION: synthetic oligonucleotide

<400> SEQUENCE: 10

```
cagattcagc tgaaggagtc tggacctgct gtcatcaagc catcacagtc actgtctctc      60
acgtgcatag tctctggatt ctccatcaca agtagtgttt attgctggca gtggatccgc     120
cagcccccag gaaagggatt agagtggatg ggacgcatct gttatgacgg ttcagttgac     180
tatagtccat ccatcacaag ccgcggcacc atctccagag acacatctct gaacaaagtc     240
tttttccagc tgagctctgt gacaaatgag gacacagcca tgtactactg ttccagggaa     300
aaccatattg attactacga tactacttat ccgtccttcg atgtctgggg cgcagggacc     360
acggtcaccg tctcctca                                                  378
```

<210> SEQ ID NO 11
<211> LENGTH: 19
<212> TYPE: PRT
<213> ORGANISM: Artificial Sequence
<220> FEATURE:
<223> OTHER INFORMATION: synthetic peptide

<400> SEQUENCE: 11

Ser Gly Ser Gly Gly Trp Leu Leu Ser Pro Arg Gly Ser Arg Pro Ser
1               5                   10                  15

Trp Gly Pro

<210> SEQ ID NO 12
<211> LENGTH: 19
<212> TYPE: PRT
<213> ORGANISM: Artificial Sequence
<220> FEATURE:
<223> OTHER INFORMATION: synthetic peptide

<400> SEQUENCE: 12

Ser Gly Ser Gly Leu Leu Ser Pro Arg Gly Ser Arg Pro Ser Trp Gly
1               5                   10                  15

Pro Thr Asp

<210> SEQ ID NO 13
<211> LENGTH: 19
<212> TYPE: PRT
<213> ORGANISM: Artificial Sequence
<220> FEATURE:
<223> OTHER INFORMATION: synthetic peptide

<400> SEQUENCE: 13

Ser Gly Ser Gly Ser Pro Arg Gly Ser Arg Pro Ser Trp Gly Pro Thr
1               5                   10                  15

Asp Pro Arg

<210> SEQ ID NO 14
<211> LENGTH: 19
<212> TYPE: PRT
<213> ORGANISM: Artificial Sequence
<220> FEATURE:
<223> OTHER INFORMATION: synthetic peptide

```
<400> SEQUENCE: 14

Ser Gly Ser Gly Arg Gly Ser Arg Pro Ser Trp Gly Pro Thr Asp Pro
1               5                   10                  15

Arg Arg Arg

<210> SEQ ID NO 15
<211> LENGTH: 19
<212> TYPE: PRT
<213> ORGANISM: Artificial Sequence
<220> FEATURE:
<223> OTHER INFORMATION: synthetic peptide

<400> SEQUENCE: 15

Ser Gly Ser Gly Ser Arg Pro Ser Trp Gly Pro Thr Asp Pro Arg Arg
1               5                   10                  15

Arg Ser Arg

<210> SEQ ID NO 16
<211> LENGTH: 19
<212> TYPE: PRT
<213> ORGANISM: Artificial Sequence
<220> FEATURE:
<223> OTHER INFORMATION: synthetic peptide

<400> SEQUENCE: 16

Ser Gly Ser Gly Pro Ser Trp Gly Pro Thr Asp Pro Arg Arg Arg Ser
1               5                   10                  15

Arg Asn Leu

<210> SEQ ID NO 17
<211> LENGTH: 19
<212> TYPE: PRT
<213> ORGANISM: Artificial Sequence
<220> FEATURE:
<223> OTHER INFORMATION: synthetic peptide

<400> SEQUENCE: 17

Ser Gly Ser Gly Trp Gly Pro Thr Asp Pro Arg Arg Arg Ser Arg Asn
1               5                   10                  15

Leu Gly Lys

<210> SEQ ID NO 18
<211> LENGTH: 19
<212> TYPE: PRT
<213> ORGANISM: Artificial Sequence
<220> FEATURE:
<223> OTHER INFORMATION: synthetic peptide

<400> SEQUENCE: 18

Ser Gly Ser Gly Pro Thr Asp Pro Arg Arg Arg Ser Arg Asn Leu Gly
1               5                   10                  15

Lys Val Ile

<210> SEQ ID NO 19
<211> LENGTH: 15
<212> TYPE: PRT
<213> ORGANISM: Artificial Sequence
<220> FEATURE:
<223> OTHER INFORMATION: synthetic peptide

<400> SEQUENCE: 19

Gly Trp Leu Leu Ser Pro Arg Gly Ser Arg Pro Ser Trp Gly Pro
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: synthetic peptide

<400> SEQUENCE: 20

Leu Leu Ser Pro Arg Gly Ser Arg Pro Ser Trp Gly Pro Thr Asp
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic peptide

<400> SEQUENCE: 21

Ser Pro Arg Gly Ser Arg Pro Ser Trp Gly Pro Thr Asp Pro Arg
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetid peptide

<400> SEQUENCE: 22

Arg Gly Ser Arg Pro Ser Trp Gly Pro Thr Asp Pro Arg Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic peptide

<400> SEQUENCE: 23

Ser Arg Pro Ser Trp Gly Pro Thr Asp Pro Arg Arg Arg Ser Arg
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic peptide

<400> SEQUENCE: 24

Ser Pro Arg Gly Ser Arg Pro Ser Trp Gly Pro Thr Asp Pro Arg
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: synthetic peptide

<400> SEQUENCE: 25

Arg Gly Ser Arg Pro Ser Trp Gly Pro Thr Asp Pro Arg Arg Arg
1               5                   10                  15

```
<210> SEQ ID NO 26
<211> LENGTH: 15
<212> TYPE: PRT
<213> ORGANISM: Artificial Sequence
<220> FEATURE:
<223> OTHER INFORMATION: synthetic peptide

<400> SEQUENCE: 26

Ser Arg Pro Ser Trp Gly Pro Thr Asp Pro Arg Arg Arg Ser Arg
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: synthetic peptide

<400> SEQUENCE: 27

Pro Ser Trp Gly Pro Thr Asp Pro Arg Arg Arg Ser Arg Asn Leu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: synthetic peptide

<400> SEQUENCE: 28

Trp Gly Pro Thr Asp Pro Arg Arg Arg Ser Arg Asn Leu Gly Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: synthetic peptide

<400> SEQUENCE: 29

Pro Thr Asp Pro Arg Arg Arg Ser Arg Asn Leu Gly Lys Val Ile
1               5                   10                  15

<210> SEQ ID NO 30
<211> LENGTH: 23
<212> TYPE: PRT
<213> ORGANISM: Artificial Sequence
<220> FEATURE:
<223> OTHER INFORMATION: synthetic peptide

<400> SEQUENCE: 30

Gly Ser Arg Pro Ser Trp Gly Pro Thr Asp Pro Arg His Arg Ser Arg
1               5                   10                  15

Asn Val Gly Lys Val Ile Asp
            20

<210> SEQ ID NO 31
<211> LENGTH: 23
<212> TYPE: PRT
<213> ORGANISM: Artificial Sequence
<220> FEATURE:
<223> OTHER INFORMATION: synthetic peptide

<400> SEQUENCE: 31

Gly Ser Arg Pro Ser Trp Gly Pro Asn Asp Pro Arg His Arg Ser Arg
```

```
1               5                   10                  15

Asn Val Gly Lys Val Ile Asp
            20

<210> SEQ ID NO 32
<211> LENGTH: 23
<212> TYPE: PRT
<213> ORGANISM: Artificial Sequence
<220> FEATURE:
<223> OTHER INFORMATION: synthetic peptide

<400> SEQUENCE: 32

Gly Ser Arg Pro Ser Trp Gly Pro Ser Asp Pro Arg His Arg Ser Arg
1               5                   10                  15

Asn Val Gly Lys Val Ile Asp
            20

<210> SEQ ID NO 33
<211> LENGTH: 11
<212> TYPE: PRT
<213> ORGANISM: Artificial Sequence
<220> FEATURE:
<223> OTHER INFORMATION: synthetic peptide

<400> SEQUENCE: 33

Arg Gly Ser Arg Pro Ser Trp Gly Pro Thr Asp
1               5                   10

<210> SEQ ID NO 34
<211> LENGTH: 11
<212> TYPE: PRT
<213> ORGANISM: Artificial Sequence
<220> FEATURE:
<223> OTHER INFORMATION: synthetic peptide

<400> SEQUENCE: 34

Arg Gly Ser Arg Pro Ser Trp Gly Pro Asn Asp
1               5                   10

<210> SEQ ID NO 35
<211> LENGTH: 13
<212> TYPE: PRT
<213> ORGANISM: Artificial Sequence
<220> FEATURE:
<223> OTHER INFORMATION: synthetic peptide

<400> SEQUENCE: 35

Leu Ser Pro Arg Gly Ser Arg Pro Ser Trp Gly Pro Thr
1               5                   10

<210> SEQ ID NO 36
<211> LENGTH: 25
<212> TYPE: PRT
<213> ORGANISM: Artificial Sequence
<220> FEATURE:
<223> OTHER INFORMATION: synthetic peptide

<400> SEQUENCE: 36

Ser Pro Arg Gly Ser Arg Pro Ser Trp Gly Pro Thr Asp Pro Arg Arg
1               5                   10                  15

Arg Ser Arg Asn Leu Gly Lys Val Ile
            20                  25

<210> SEQ ID NO 37
<211> LENGTH: 5
```

```
<212> TYPE: PRT
<213> ORGANISM: Artificial Sequence
<220> FEATURE:
<223> OTHER INFORMATION: synthetic peptide

<400> SEQUENCE: 37

Gly Pro Thr Asp Pro
1               5
```